(12) United States Patent
Patel

(10) Patent No.: US 7,816,518 B2
(45) Date of Patent: Oct. 19, 2010

(54) PORPHYRIN DERIVATIVES AND THEIR USE IN PHOTON ACTIVATION THERAPY

(75) Inventor: Bipin Chandra Muljibhai Patel, Guildford (GB)

(73) Assignee: Psimei Pharmaceuticals, PLC, Guildford, Surrey (GB)

( * ) Notice: Subject to any disclaimer, the term of this patent is extended or adjusted under 35 U.S.C. 154(b) by 176 days.

(21) Appl. No.: 11/632,106

(22) PCT Filed: Jul. 8, 2005

(86) PCT No.: PCT/GB2005/002693
§ 371 (c)(1), (2), (4) Date: Jul. 12, 2007

(87) PCT Pub. No.: WO2006/005924
PCT Pub. Date: Jan. 19, 2006

(65) Prior Publication Data
US 2008/0039436 A1 Feb. 14, 2008

(30) Foreign Application Priority Data
Jul. 13, 2004 (GB) ................................. 0415663.4

(51) Int. Cl.
C07B 47/00 (2006.01)
C07D 487/22 (2006.01)
(52) U.S. Cl. ..................................................... 540/145
(58) Field of Classification Search .................. 540/145
See application file for complete search history.

(56) References Cited
U.S. PATENT DOCUMENTS

| 4,959,356 A | 9/1990 | Miura et al. | 514/64 |
| 5,877,165 A | 3/1999 | Miura et al. | 514/64 |

FOREIGN PATENT DOCUMENTS

| EP | 0704447 A1 | 4/1996 |
| WO | WO02/096366 A2 | 12/2002 |
| WO | WO-02098417 A1 | 12/2002 |
| WO | WO-2004046151 A2 | 6/2004 |
| WO | WO-2006005924 A1 | 1/2006 |
| WO | WO-2006016943 A1 | 2/2006 |

OTHER PUBLICATIONS

Gassman et al., "Electronic Effects of Peripheral . . . ", J. Am. Chem. Soc., 1992, 114, 9990-10000.*
Samuels et al., "Halogenation of porphyrin . . . ", J. Chem. Soc., 1968, 145-147.*
Osterloh and Vicente, 2002, "Mechanisms of porphyrinoid localization in tumors," *J. Porphyrins and Phthalocyanines*, 6:305-24.
Gassman, et al., "Electronic Effects of Peripheral Substituents in Porphyrins: X-ray Photoelectron Spectroscopy and ab Initio Self-Consistent Field Calculations", J. Am. Chem. Soc. (1992), v. 114, pp. 9990-1000.
Samuels, et al., "Halogenation of Porphin and Octaethylporphin", J. Chem. Soc. (1968), No. 2, pp. 145-147.
International Search Report (PCT/GB2005/002693) Sep. 30, 2005.

* cited by examiner

*Primary Examiner*—James O. Wilson
*Assistant Examiner*—Paul V. Ward
(74) *Attorney, Agent, or Firm*—Brenda Herschbach Jarrell; Charles E. Lyon; Choate, Hall & Stewart LLP

(57) ABSTRACT

The present invention relates to the use of a compound of formula (I) in the manufacture of a pharmaceuticals composition for cell death by photo activation therapy and the use of the compounds in the prevention and/or treatment of cancer.

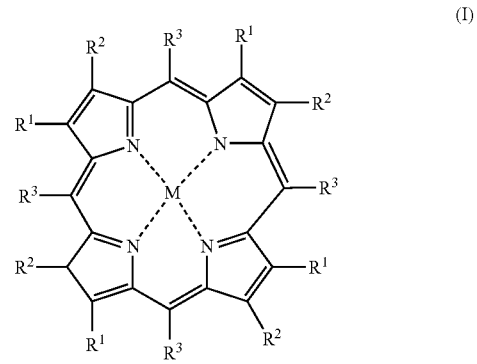

(I)

22 Claims, 1 Drawing Sheet

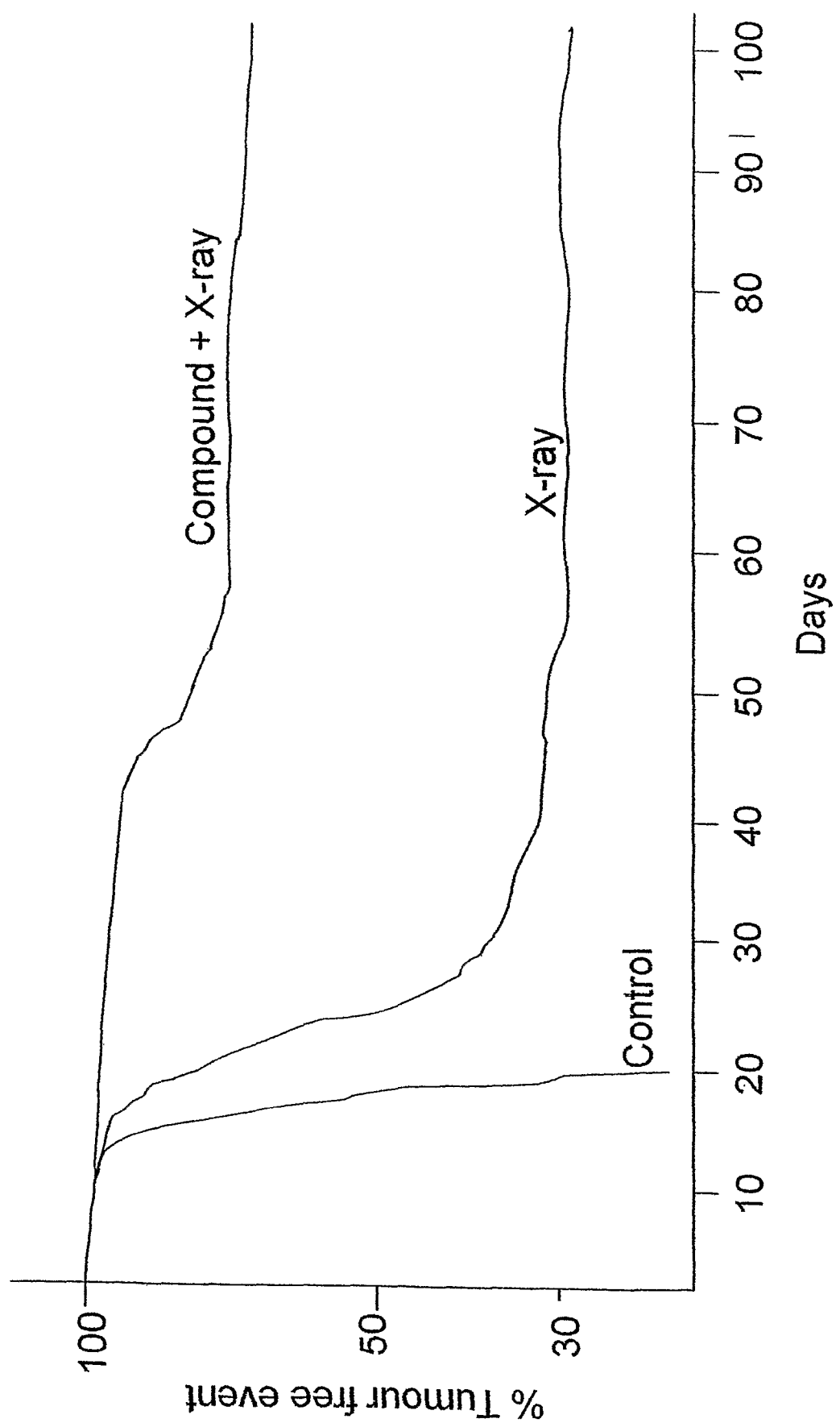

PORPHYRIN DERIVATIVES AND THEIR USE IN PHOTON ACTIVATION THERAPY

The present application claims the benefit under 35 U.S.C. §371 of International Application No. PCT/GB2005/002693 (published PCT application No. WO 2006/005924), filed Jul. 8, 2005, which claims priority to Great Britain Application No. GB 0415663.4, filed Jul. 13, 2004. The entire contents of each of the above-referenced applications are incorporated herein by reference.

The present invention provides improved compounds for photon activation therapy and their use in killing target cells such as tumours. The means and methods of the present invention enable optimisation of photon activation therapy for clinical use.

A number of different bimodal therapies are used in the treatment of cancer. These therapies normally entail two steps wherein firstly a pharmaceutically inactive agent is administered to a patient and allowed to reach its target site within in the body. Secondly the inactive species is activated to a toxic species which kills the target cell. Such bimodal therapies known in the art include photodynamic therapy (PDT), boron neutron capture therapy (BNCT), and radiosensitization. The use of these bimodal therapies provide advantages over convention radiotherapy wherein the biological effect of the therapy is spread over the entire irradiated area and a high radiation dose is required to generate the destructive ionisation tracks to produce the desired biological effect.

Photon activation therapy is a form of radiosensitization. It generally uses a pharmaceutically inert agent which accumulates in the target cells. The agent is activated in vivo using X-rays by irradiation of the target cells and surrounding tissue.

Gadolinium teaxfrin has been developed for the treatment of brain tumours using photon activation therapy. Whole brain irradiation is used to activate the agent and the patients are monitored for neurological progression. Activation of gadolinium teaxfrin with ionising radiation produces a short lived cytotoxic radical which is highly damaging to cells and cellular organelles. There is therefore a need in the art for a photon activation therapy agent which can be used while minimising unwanted damage to the surrounding cells and tissues.

Porphyrins have previously been used in medicine. These compounds show high affinity to neoplastic tissues of mammals and have been used in PDT. The use of the porphyrins clinically has been limited, however, by the poor penetration of the visible light required to activate the porphyrins.

The present invention provides porphyrin derivatives which can be activated by ionising radiation in vivo to provide a stable long life radical. The halogenated porphyrins exhibit changes in their conformations and photophysical and chemical properties. For example, the substitution of meso-tetraphenylporphyrin with eight bromide atoms at the pyrrole rings generates a oxidation potential shift by 550 mV. It is postulated that this increase in oxidation potential provides enhanced stability towards oxidative degradation for halogenated porphyrins allowing them to be used in photon activation therapy. These porphyrins can be used as catalysts or non-linear absorbing materials. The production of such a stable long life radical reduces the amount of damaging irradiation required to activate the agent. The agent can also be provided in a lower concentration than that required for other techniques such as BNCT. The use of the compounds of the present invention provide a number of advantages in vivo as they exhibit low systemic toxicity, high selectivity for a tumour, and rapid clearance from the blood. Furthermore, the halogenated prophyrins show improved potency when combined with x-rays and exhibit selectivity for tumour tissues.

The first aspect of the invention therefore provides the use of a compound of formula (I)

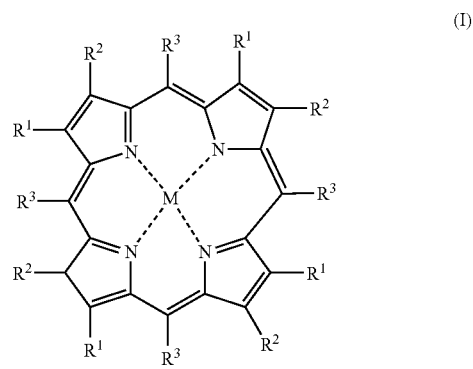

in the manufacture of a pharmaceutical composition for cell death by photon activation therapy;

wherein each $R^1$ is independently selected from hydrogen, optionally substituted $C_{1-8}$ alkyl, optionally substituted $C_{2-8}$ alkenyl, halide, $SO_3R^4$, =O or $NO_2$, wherein the substituents are selected from one or more of $C_{1-6}$ alkyl, $R^5$, =O, $OR^5$, $CO_2R^5$, $CONR^6R^6$, and each substituent may further be substituted with one or more of $CO_2R^5$ or $OR^5$;

wherein each $R^2$ is independently selected from hydrogen, optionally substituted $C_{1-8}$ alkyl, optionally substituted $C_{2-6}$ alkenyl, halide, $SO_3R^4$, $NO_2$, wherein the substituents are selected from one or more of $C_{1-6}$ alkyl, $R^5$, =O, $OR^5$, $CO_2R^5$, $CONR^6R^6$, and each substituent may further be substituted with one or more of $CO_2R^5$ or $OR^5$;

and wherein the $C_{1-8}$ alkyl group can be optionally interrupted with one or more of O, $CO_2$ or $NR^7$;

wherein $R^1$ and $R^2$ may together form a six membered ring, wherein said ring can be fully saturated, partially saturated or unsaturated and is optionally substituted with one or more of =O, halide, $SO_3R^4$, $NO_2$, $C_{1-6}$ alkyl or $CO_2R^5$;

wherein each $R^3$ is independently hydrogen, halide, $C_{1-20}$ alkyl, $C_{2-20}$ alkenyl, $C_{2-20}$ alkynyl, $C_{1-6}$ haloalkyl, $C_{3-12}$ aryl or $C_{3-12}$ heteroaryl, $C_{1-20}$ alkyloxy, $C_{2-20}$ alkenyloxy, $C_{2-20}$ alkynyloxy, $C_{3-12}$ aryloxy, $C_{3-12}$ heteroaryloxy; wherein the alkyl, alkoxy, alkenyl, alkenyloxy, alkynyl, alkynyloxy, aryl, aryloxy, heteroaryl and heteroaryloxy group are optionally substituted with one or more of $C_{1-6}$ alkyl, aryl, $R^5$, $OR^5$, $NR^6_2$, $SO_3R^4$, $NO_2$, halide, $CO_2R^5$ or $B(OR^6)_2$ and each substituent may be further substituted with one or more of halide, $C_{1-6}$ alkyl;

wherein $R^2$ and $R^3$, or $R^1$ and $R^3$ may together form a five membered ring, wherein said ring can be fully saturated, partially saturated or unsaturated and is optionally substituted with one or more of =O, $C_{1-8}$ alkyl, or $CO_2R^5$;

wherein one or more of $R^1$, $R^2$ or $R^3$ is an electron withdrawing group selected from F, Cl, Br, I, $NO_2$, preferably Br;

wherein $R^4$ is hydrogen or $C_{1-6}$ alkyl; $R^5$ is hydrogen or $C_{1-6}$ alkyl, $C_{6-12}$ aryl, optionally substituted carborane, a biocompatible polymer or a counter ion such as Na or K, said alkyl or aryl groups being optionally substituted with $NR^6_2$, $NO_2$, $C_{1-4}$ alkyl or $C_{6-12}$ aryl; $R^6$ is hydrogen or $C_{1-6}$ alkyl, $R^7$ is hydrogen or $C_{1-6}$ alkyl optionally substituted with $CO_2R^5$;

and M is a metal or hydrogen, preferably selected from V, Ga, Mn, Fe, Ru, Tc, Cr, Pt, Co, Ni, Cu, Zn, Ge, In, Sn, Y, Au, Ba, W, Gd, Pb, or Pt. In a preferred feature of the first aspect the metal is Au or Pb or any other metal which generates a shower of electrons on irradiation with x-rays. The generation of said shower of electrons increases the potency of the compounds of the invention.

In a preferred feature of the first aspect, one or more of the $R^1$ groups is an electron with-drawing group such as a halide or $NO_2$ preferably a halide selected from F, Cl, Br or I, more preferably Br or Cl, most preferably Br. More preferably 2, 3 or 4 of the $R^1$ groups is a halide. It would be understood by a person skilled in the art that $R^1$ can be any electron withdrawing group, wherein the $R^1$ group preferably provides the same degree of electronegativity as a halide group.

In a further preferred feature of the first aspect, one or more of the $R^2$ groups is an electron with-drawing group preferably a halide selected from F, Cl, Br or I, more preferably Br or Cl, most preferably Br. More preferably 2, 3 or 4 of the $R^2$ groups is a halide.

In a further preferred feature of the first aspect, one or more of the $R^3$ groups is an electron with-drawing group preferably a halide selected from F, Cl, Br or I, more preferably Br or Cl, most preferably Br. More preferably 2, 3 or 4 of the $R^3$ groups is a halide.

In a preferred feature of the first aspect, one or more of the $R^1$ groups and one or more of the $R^2$ groups is an electron with-drawing group preferably a halide selected from F, Cl, Br or I, more preferably Br or Cl, most preferably Br. More preferably 2, 3 or 4 of the $R^1$ groups and 2, 3, or 4 of the $R^2$ groups is a halide.

In a more preferred feature of the first aspect, the compound of the invention is substituted with 4, 5, 6, 7, 8, 9 or 10 halide atoms, preferably 8 halide atoms, wherein said halide atoms are preferably Br.

For the purposes of this invention, alkyl relates to both straight chain and branched alkyl radicals of 1 to 20 carbon atoms, preferably 1 to 8 carbon atoms, more preferably 1 to 6 carbon atoms, most preferably 1 to 4 carbon atoms including but not limited to methyl, ethyl, n-propyl, isopropyl, n-butyl, sec-butyl, isobutyl, tert-butyl. The term alkyl also encompasses cycloalkyl radicals including but not limited to cyclopropyl, cyclobutyl, $CH_2$-cyclopropyl, $CH_2$-cyclobutyl.

Haloalkyl relates to an alkyl radical preferably having 1 to 8 carbon atoms, preferably 1 to 4 carbon atoms substituted with one or more halide atoms for example $CH_2CH_2Br$, $CF_3$ or $CCl_3$.

The term "alkenyl" means a straight chain or branched alkylenyl radical of 2 to 20 carbon atoms, preferably 2 to 8, more preferably 2 to 6 carbon atoms, most preferably 2 to 4 carbon atoms, and containing one or more carbon-carbon double bonds and includes but is not limited to ethylene, n-propyl-1-ene, n-propyl-2-ene, isopropylene, etc. "Alkynyl" means a straight chain or branched chain alkynyl radical of 2 to 20 carbon atoms, preferably 2 to 8 carbon atoms, more preferably 2 to 6 carbon atoms, most preferably 2 to 4 carbon atoms, including but not limited to ethynyl, 2-methylethynyl. The alkyl, alkenyl and/or alkynyl radicals of the invention can comprise 1, 2, 3, 4, 5, 6, 7, 8, 9, 10, 11, 12, 13, 14, 15, 16, 17, 18, 19 or 20 carbon atoms.

"Aryl" means an aromatic 3-12 membered hydrocarbon preferably a 5 or 6-membered hydrocarbon containing one ring or being fused to one or more saturated or unsaturated rings including but not limited to phenyl, napthyl, anthracenyl or phenanthracenyl.

"Heteroaryl" means an aromatic 3-12 membered aryl preferably a 5- or 6-membered hydrocarbon containing one or more heteroatoms selected from N, O or S and containing one ring or being fused to one or more saturated or unsaturated rings. The heteroaryl can be fully saturated, partially saturated or unsaturated. Examples of aryl or heteroaryl groups include but are not limited to phenyl, acridine, benzimidazole, benzofuran, benzothiophene, benzoxazole, benzothiazole, carbazole, cinnoline, dioxin, dioxane, dioxolane, dithiane, dithiazine, dithiazole, dithiolane, furan, imidazole, imidazoline, imidazolidine, indole, indoline, indolizine, indazole, isoindole, isoquinoline, isoxazole, isothiazole, morpholine, napthyridine, oxazole, oxadiazole, oxathiazole, oxathiazolidine, oxazine, oxadiazine, phenazine, phenothiazine, phenoxazine, phthalazine, piperazine, piperidine, pteridine, purine, pyran, pyrazine, pyrazole, pyrazoline, pyrazolidine, pyridazine, pyridine, pyrimidine, pyrrole, pyrrolidine, pyrroline, quinoline, quinoxaline, quinazoline, quinolizine, tetrahydrofuran, tetrazine, tetrazole, thiophene, thiadiazine, thiadiazole, thiatriazole, thiazine, thiazole, thiomorpholine, thianaphthalene, thiopyran, triazine, triazole, or trithiane.

Halogen means F, Cl, Br or I, preferably Br or Cl.

In a preferred feature of the first aspect, the group $R^5$ is a biocompatible polymer. The presence of the biocompatible polymers allows the physical and chemical properties of the compound of the invention to be varied. The presence of such biocompatible polymers may for example enhance water solubility, enhance tumour targeting, reduce the toxicity profile, for example by reducing and/or preventing interference with blood cells and/or platelets or by reducing accumulation of the compound in the liver, spleen, bone marrow and/or lungs. Examples of such biocompatible polymers include one or more of N-(2-hydroxypropyl)methacrylamide (HPMA Copolymer)-pendant chain, polyethylene glycol (PEG), ethyleneglycol copolymers, polysaccharides e.g. Dextrin, Dextran chitosan (N-succinyl chitosan), carboxymethyl chitin, carboxymethyl pullulan, alginate, poly(amino acids), poly [N-(2-hydroxyethyl)-L-glutamine) PHEG, β-poly(2-hydroxyethyl aspartamide) PHEA, poly(glutamic acid), poly (aspartic acid), polylysine (poly(L-lysine) polyesters, poly(α or β-malic acid), alternating polymers, PEG-lysine, block copolymers, poly(ethylene glycol-aspartate), copolymers of styrene and maleic anhydride, polygalacturonic acid, copolymers of hydroxyalkyl(meth)acrylate e.g. N-phenylpyrrolidone, poly(L-glutamic acid and hydroxyethyl-L-glutamine), poly(α-malic acid), polyaspartic acid-PEG copolymers, poly-L-lysine and copolymers of polyethyleneimine, poly(α-L-glutamic acid) (PGA), biodegradable diamido-diamine polymer or steroids such as estradiol, or cholesterol. $R^5$ may also be a carborane optionally substituted with one or more of $C_{1-4}$ alkyl, OH, $NH_2$ or halide.

It will be appreciated by a person skilled in the art that the compounds of the invention can be derivatised with one or more biocompatible polymer and the present invention encompasses such derivatised compounds. Such derivatisation can occur at any position on the compound of formula I bearing a functional moiety. Examples of such moieties include —$CO_2H$, OH, Br, —CH=CH—, C=O, $NH_2$, etc.

In a more preferred feature of the first aspect $R^1$ is $C_{1-4}$ alkyl, more preferably methyl, or a halide more preferably Br, $R^2$ is $C_{1-4}$ alkyl optionally substituted with $CO_2R^5$, or a halide, more preferably Br, and $R^3$ is $C_{6-12}$ aryl, preferably phenyl optionally substituted with $CO_2R^5$ or $OR^5$, or a halide preferably Br, wherein $R^5$ is preferably a biocompatible polymer as defined above.

The compounds of the first aspect of invention are provided for the prevention and/or treatment of cancer, preferably wherein the cancer is a solid tumour and/or metastasis. The compounds of the invention are provided for the prevention and/or treatment of lymphomas and skin cancers. The tumour may be skin cancer such as malignant melanoma, including squamous cell carcinoma, merkel cell carcinoma, and basal cell carcinoma, lung cancer, head and neck cancer, bone cancer, prostate cancer, colon cancer, cervical cancer breast cancer, brain cancer, liver cancer or pancreatic cancer. The compounds may also be used in combination with surgery to help shrink the size of the tumour and reduce normal tissue loss.

The compound of the present invention is provided for a subject in need thereof. The subject may be a mammal, including a human or a domestic animal such as a pet, a zoo animal or a farm animal. In particular the compound can be used for the treatment of animals such as cats, dogs, horses, cattle, pigs, goats, sheep, birds, primates, elephants, or big cats.

The present invention is not restricted to the treatment of cancer by photon activation therapy, but may be used in any method which requires photon activation therapy for tissue death. For the purposes of this invention, the term "cell death" also includes tissue death. Examples of conditions which may benefit from photon activation therapy include non-malignant diseases, non-metastatic benign tumours, uterine fibroids, arthritis, breast adenoma, menohrragina, benign prostate hyperplasia and destruction of selective cardiac structures or clots. Photon activation therapy may also be used where tissue death is preferable to procedures such as surgery, photodynamic therapy, cryosurgery, thermal laser ablation and vaporisation. The compounds of the present invention are additionally provided for the treatment of other diseases such as vascular diseases such as atherosclerotic plaques, age related macular degenerative disorder.

For the purposes of this invention "cell death" encompasses both destruction and damage or impairment of cells. The term "cell death" encompasses cell ablation but for the purposes of this invention the tumour tissue or cell does not need to be removed from the body after PAT. The impairment of the cells can be permanent or temporary.

The second aspect of the invention provides a compound of formula (I)

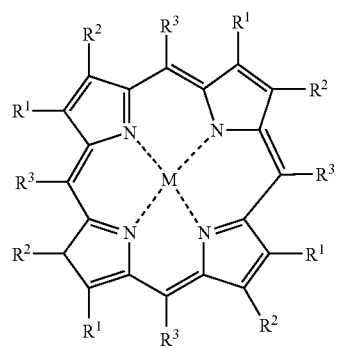

(I)

wherein each $R^1$ is independently selected from hydrogen, optionally substituted $C_{1-8}$ alkyl, optionally substituted $C_{2-8}$ alkenyl, halide, $SO_3R^4$, $NO_2$, =O, wherein the substituents are selected from one or more of $C_{1-6}$ alkyl $R^5$, =O, $OR^5$, $CO_2R^5$, $CONR^6R^6$, and each substituent may further be substituted with one or more of $CO_2R^5$ or $OR^5$;

wherein each $R^2$ is independently selected from hydrogen, optionally substituted $C_{1-8}$ alkyl, optionally substituted $C_{2-6}$ alkenyl, halide, $SO_3R^4$, $NO_2$, wherein the substituents are selected from one or more of $C_{1-6}$ alkyl, $R^5$, =O, $OR^5$, $CO_2R^5$, $CONR^6R^6$, and each substituent may further be substituted with one or more of $CO_2R^5$ or $OR^5$; and wherein the $C_{1-8}$ alkyl group can be optionally interrupted with one or more of O, $CO_2$ or $NR^7$;

wherein $R^1$ and $R^2$ may together form a six membered ring, wherein said ring can be fully saturated, partially saturated or unsaturated and is optionally substituted with one or more of =O, $C_{1-8}$ alkyl, halide, $SO_3R^4$, $NO_2$ or $CO_2R^5$;

wherein each $R^3$ is independently hydrogen, halide, $C_{1-6}$ alkyl, $C_{1-6}$ haloalkyl, $NO_2$, $C_{3-12}$ aryl, $C_{3-12}$ heteroaryl, $C_{1-6}$ alkoxy, $C_{3-12}$ aryloxy, or $C_{3-12}$ heteroaryloxy; wherein the alkyl, alkoxy, aryl, aryloxy, heteroaryl and heteroaryloxy group are optionally substituted with one or more of $C_{1-6}$ alkyl, $R^5$, $C_{3-12}$ aryl, $OR^5$, $NR^6$, $SO_3R^4$, halide, $CO_2R^5$, $B(OR^6)_2$ and each substituent may be further substituted with one or more of halide or $C_{1-6}$ alkyl;

wherein $R^2$ and $R^3$, or $R^1$ and $R^3$ may together form a five membered ring, wherein said ring can be fully saturated, partially saturated or unsaturated and is optionally substituted with one or more of =O, $C_{1-8}$ alkyl or $CO_2R^5$ wherein one or more of $R^1$, $R^2$ or $R^3$ is an electron withdrawing group selected from F, Cl, Br, I, $NO_2$, preferably Br wherein $R^4$ is hydrogen or $C_{1-6}$ alkyl; $R^5$ is hydrogen or $C_{1-6}$ alkyl or an optionally substituted carborane, a biocompatible polymer or a counter ion such as Na or K; $R^6$ is hydrogen or $C_{1-6}$ alkyl; $R^7$ is hydrogen or $C_{1-6}$ alkyl optionally substituted with $CO_2R^5$;

and M is a metal or hydrogen, preferably selected from V, Mn, Fe, Ru, Tc, Cr, Pt, Co, Ni, Cu, Zn, Ge, In, Sn, Y, Au, Ba, W, Gd, Pb, or Pt with the proviso that when $R^1$ and $R^2$ are both bromide or are both chloride, $R^3$ is not hydrogen or phenyl substituted with F, Br, $CO_2Me$, $CO_2Et$, $CH_3$, $Cf_3$, Cl or $NO_2$;

$R^1$ and $R^2$ are bromide or chloride, $R^3$ is not phenyl substituted with F, Br, $Co_2Me$, $CO_2Et$, $CH_3$, $CF_3$, Cl or $NO_2$;

$R^1$ and $R^2$ are both hydrogen, $R^3$ is not Cl, Br, F, $Cf_3$ or phenyl substituted with Cl or F;

$R^1$ is hydrogen, $R^3$ is phenyl, $R^2$ is not $NO_2$, Cl or $CH_2OH$;

$R^2$ is hydrogen, $R^1$ is $NO_2$, $R^3$ is not phenyl substituted with methyl;

$R^2$ is hydrogen, $R^1$ is F, $R^3$ is not hydrogen; and when $R^1$ and $R^2$ are both ethyl, $R^3$ is not $NO_2$.

In a preferred feature of the second aspect, one or more of the $R^1$ groups is an electron with-drawing group preferably a halide selected from F, Cl, Br or I, more preferably Br or Cl, most preferably Br. More preferably 2, 3 or 4 of the $R^1$ groups is a halide.

In a further preferred feature of the second aspect, one or more of the R groups is an electron with-drawing group preferably a halide selected from F, Cl, Br or I, more preferably Br or Cl, most preferably Br. More preferably 2, 3 or 4 of the $R^2$ groups is a halide.

In a further preferred feature of the second aspect, one or more of the $R^3$ groups is an electron with-drawing group preferably a halide selected from F, Cl, Br or I, more preferably Br or Cl, most preferably Br. More preferably 2, 3 or 4 of the $R^3$ groups is a halide.

In a preferred feature of the second aspect, one or more of the $R^1$ groups and one or more of the $R^2$ groups is an electron with-drawing group preferably a halide selected from F, Cl, Br or I, more preferably Br or Cl, most preferably Br. More preferably 2, 3 or 4 of the $R^1$ groups and 2, 3, or 4 of the $R^2$ groups is a halide.

Preferred compounds for the first and second aspects of the present invention are:

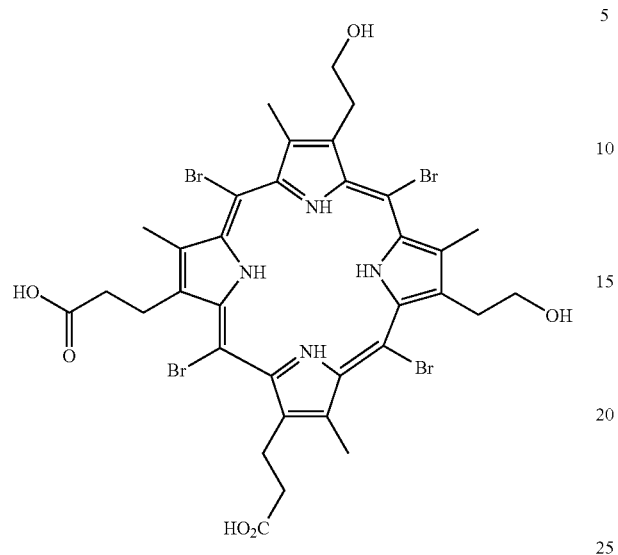
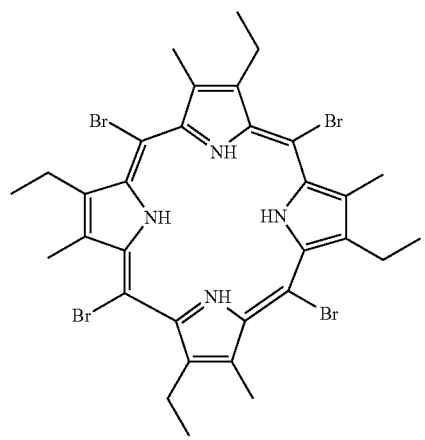
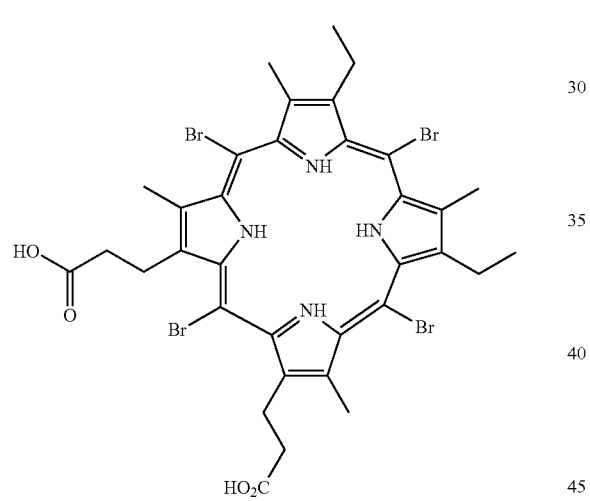
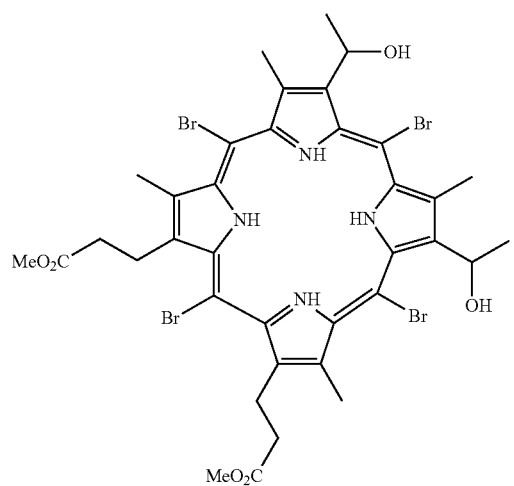
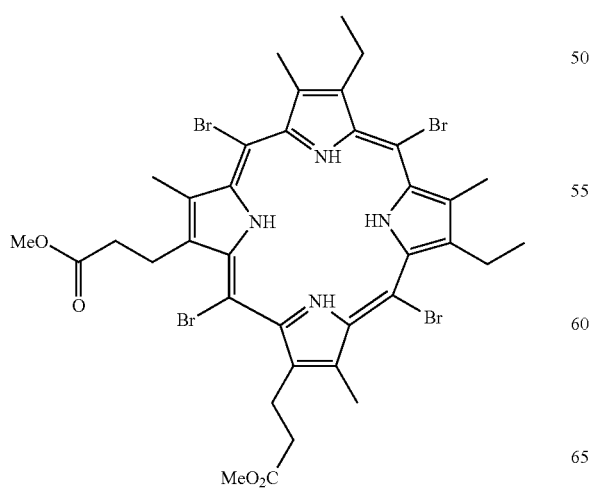
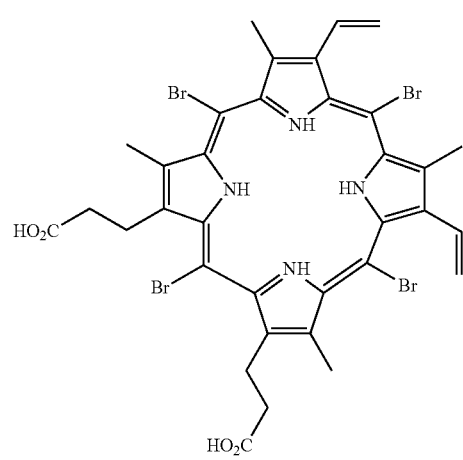

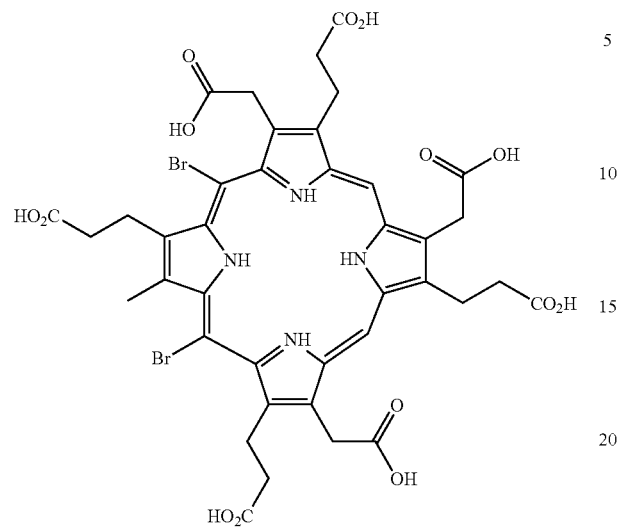
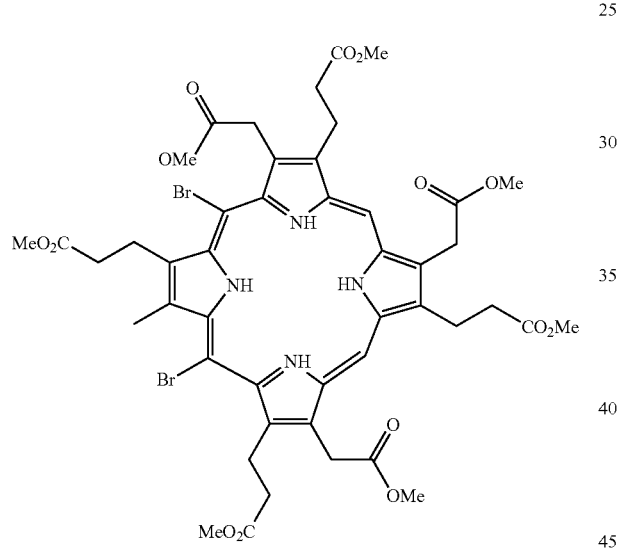
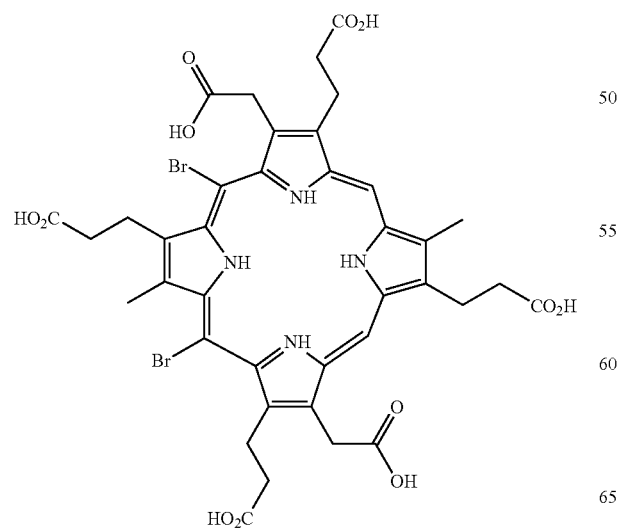
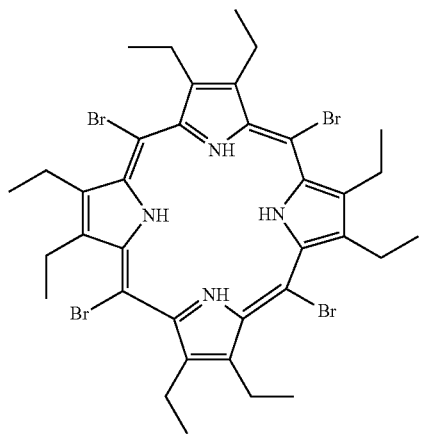
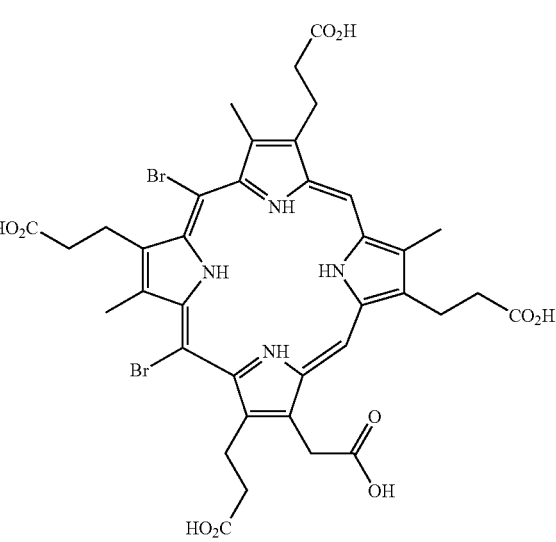
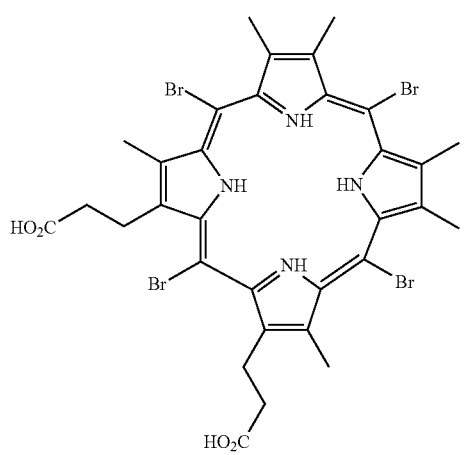

11
-continued
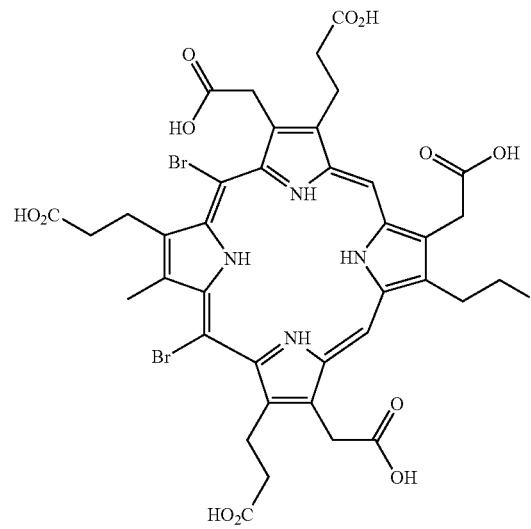
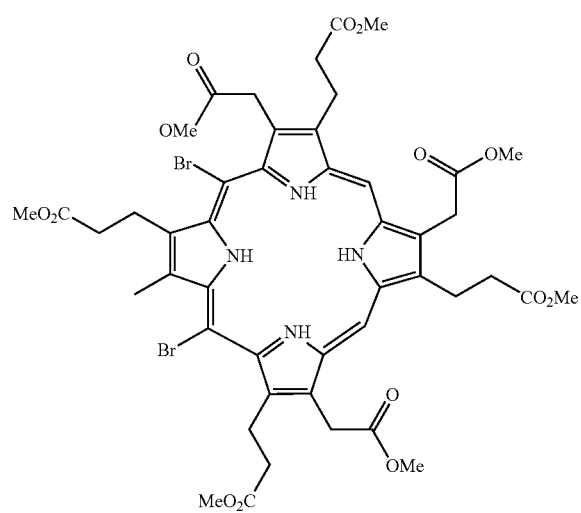
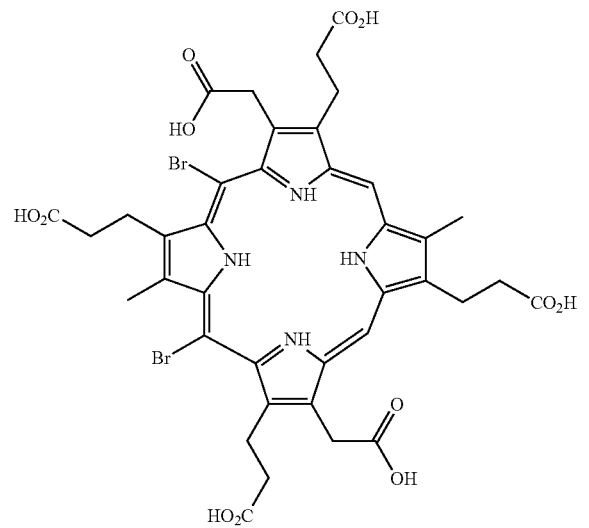
12
-continued
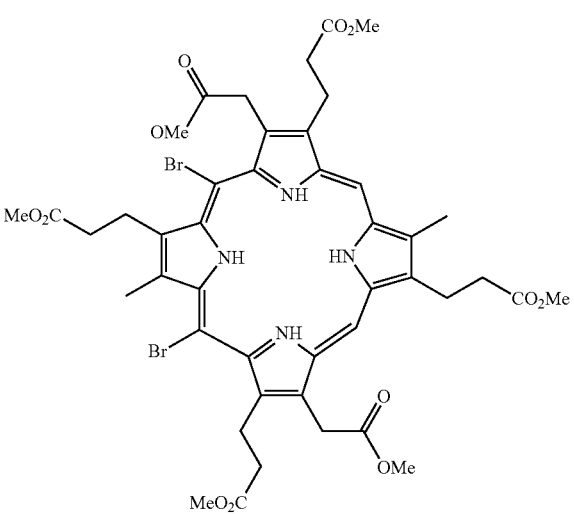
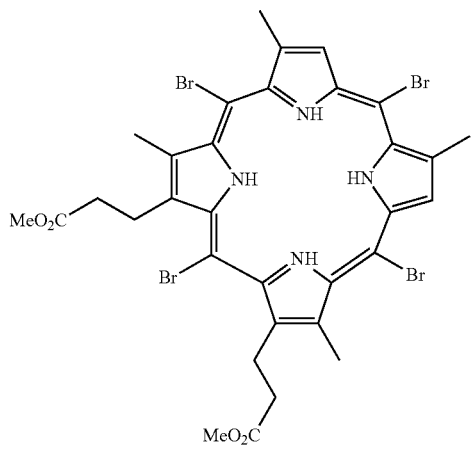
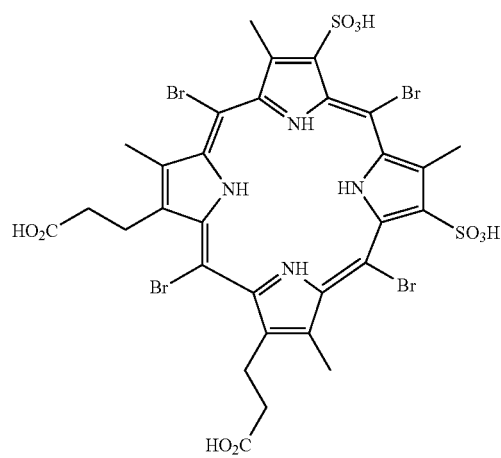

-continued
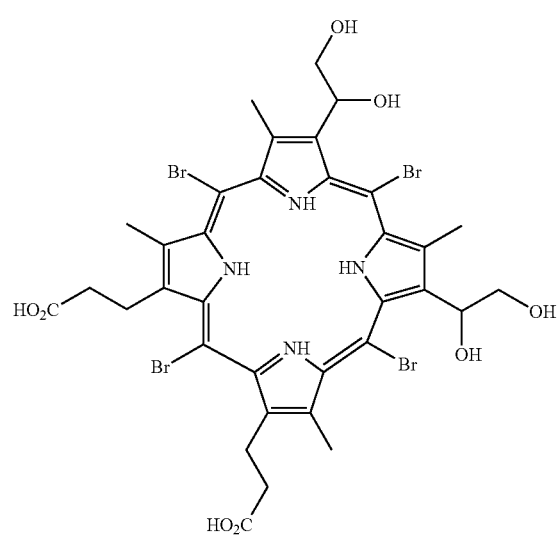
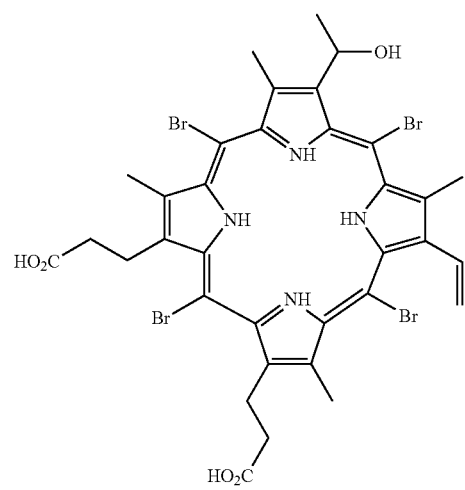
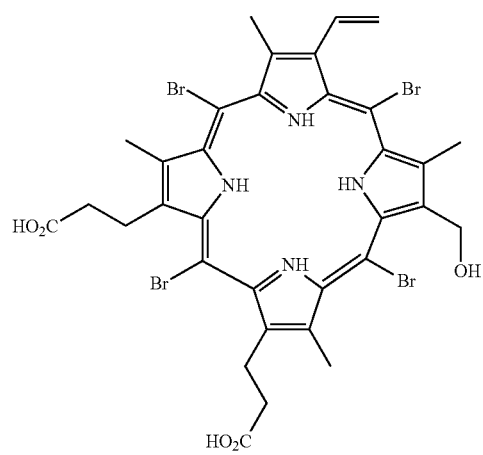
-continued
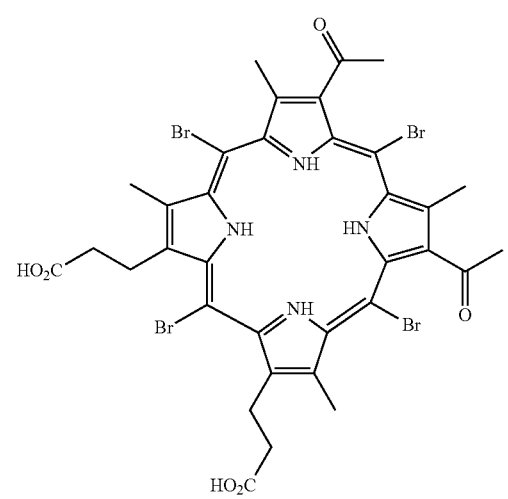
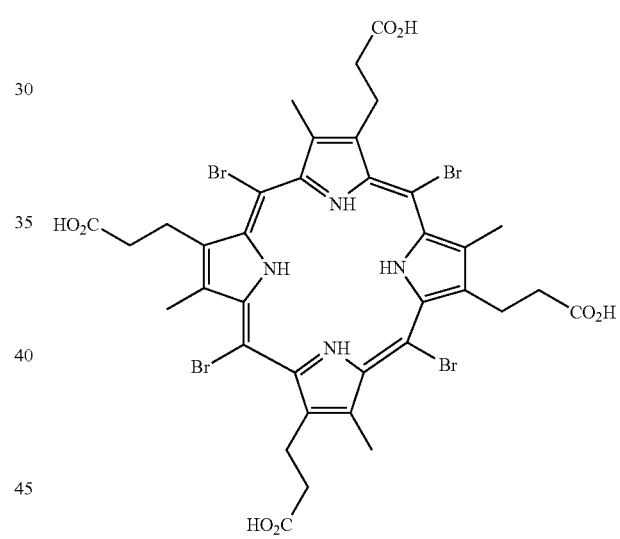
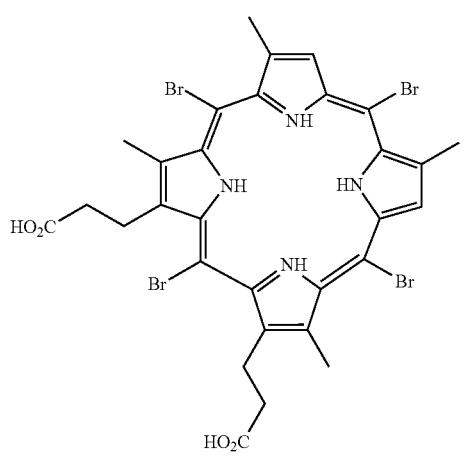

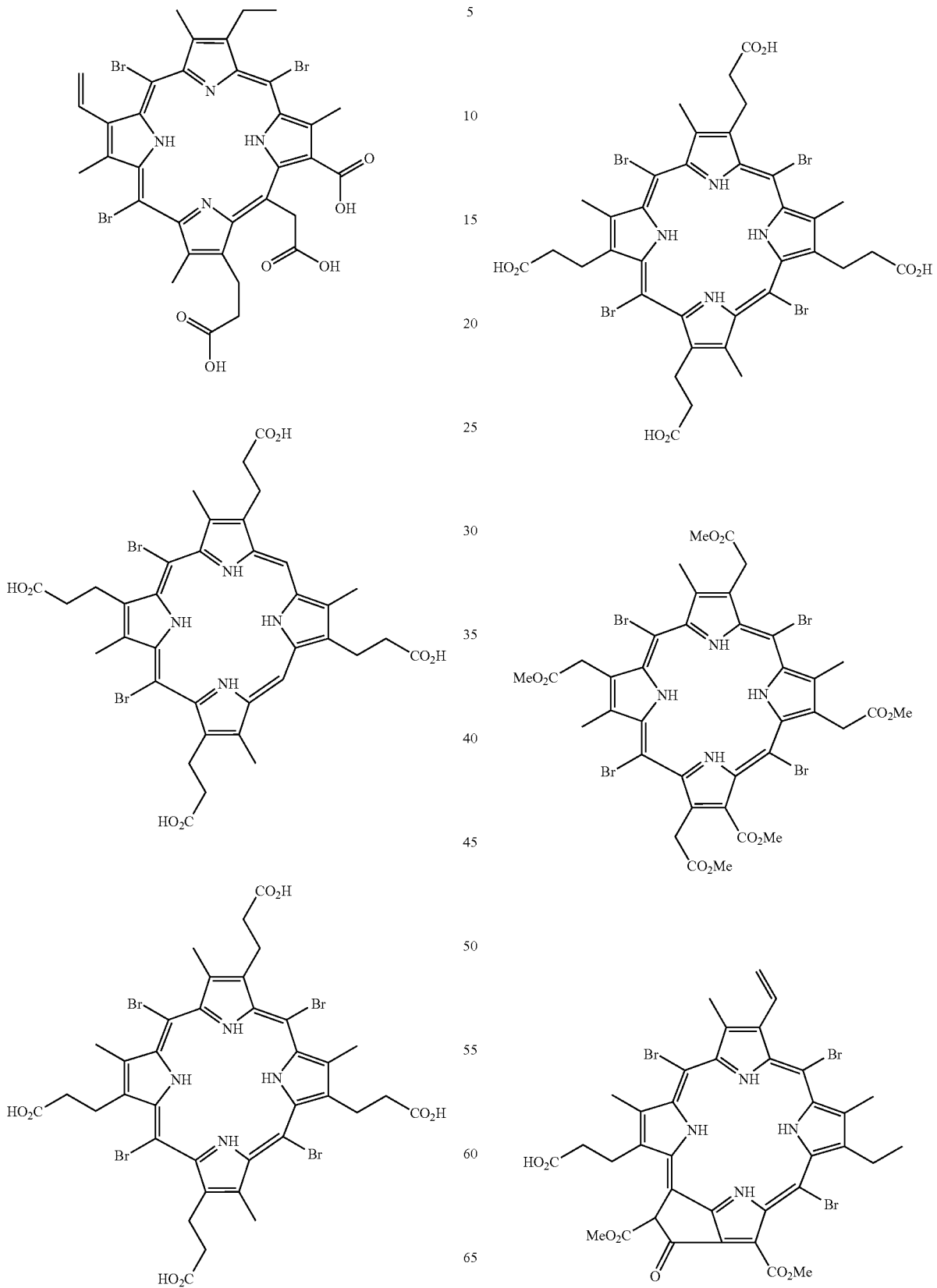

-continued
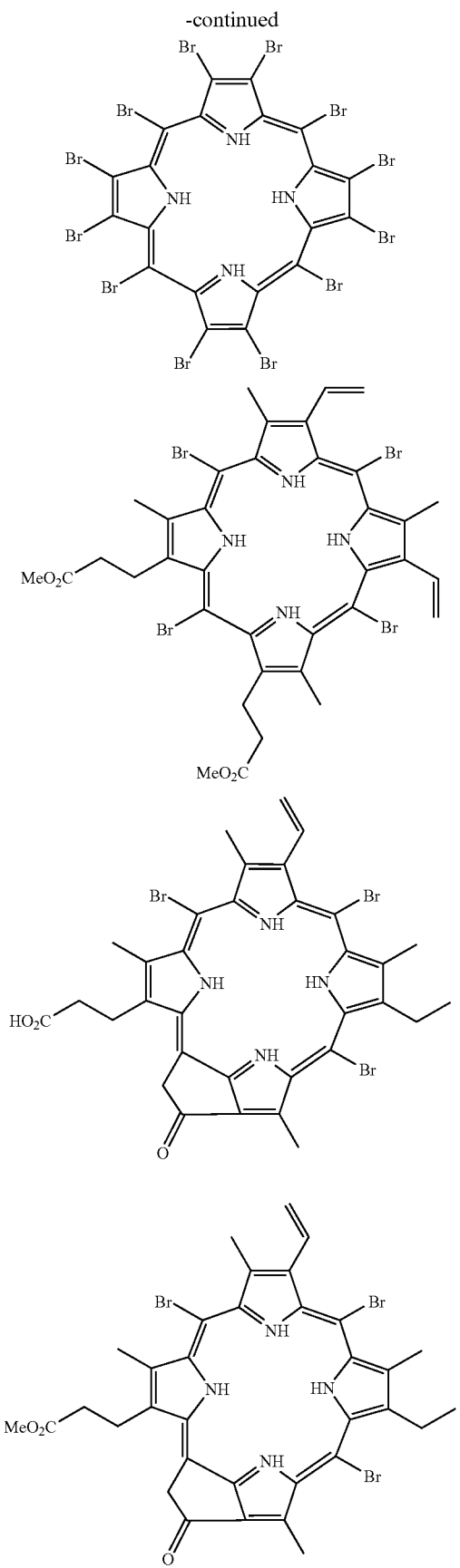
-continued
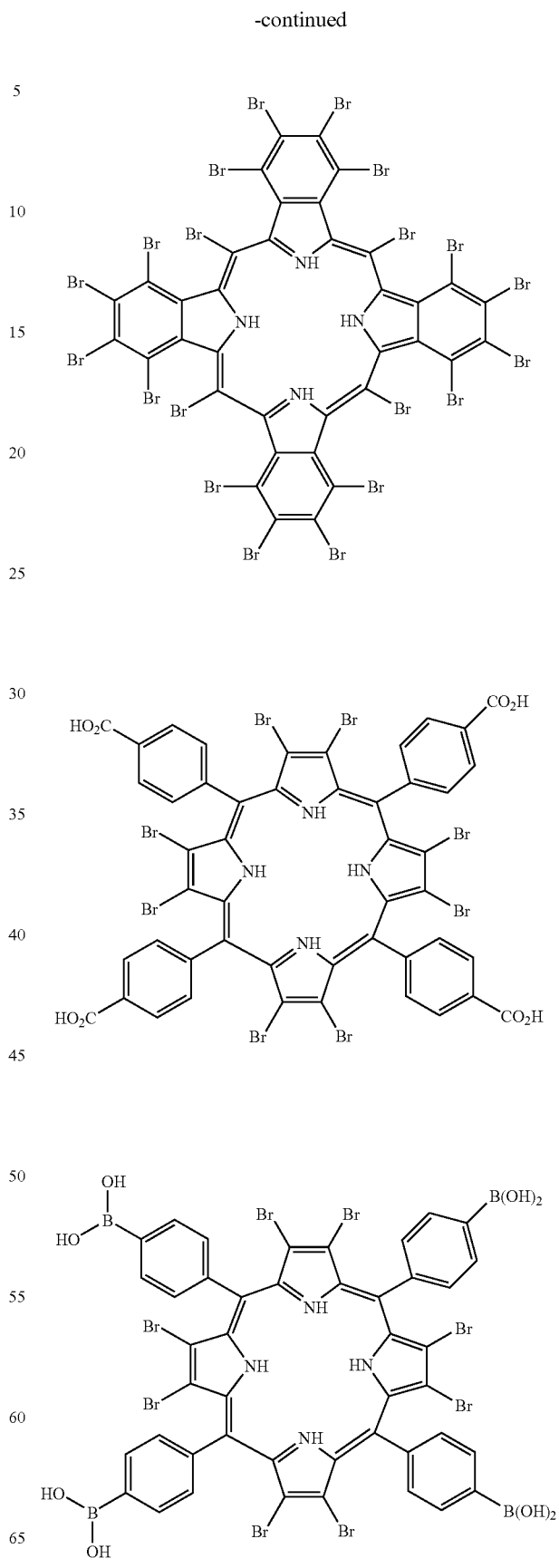

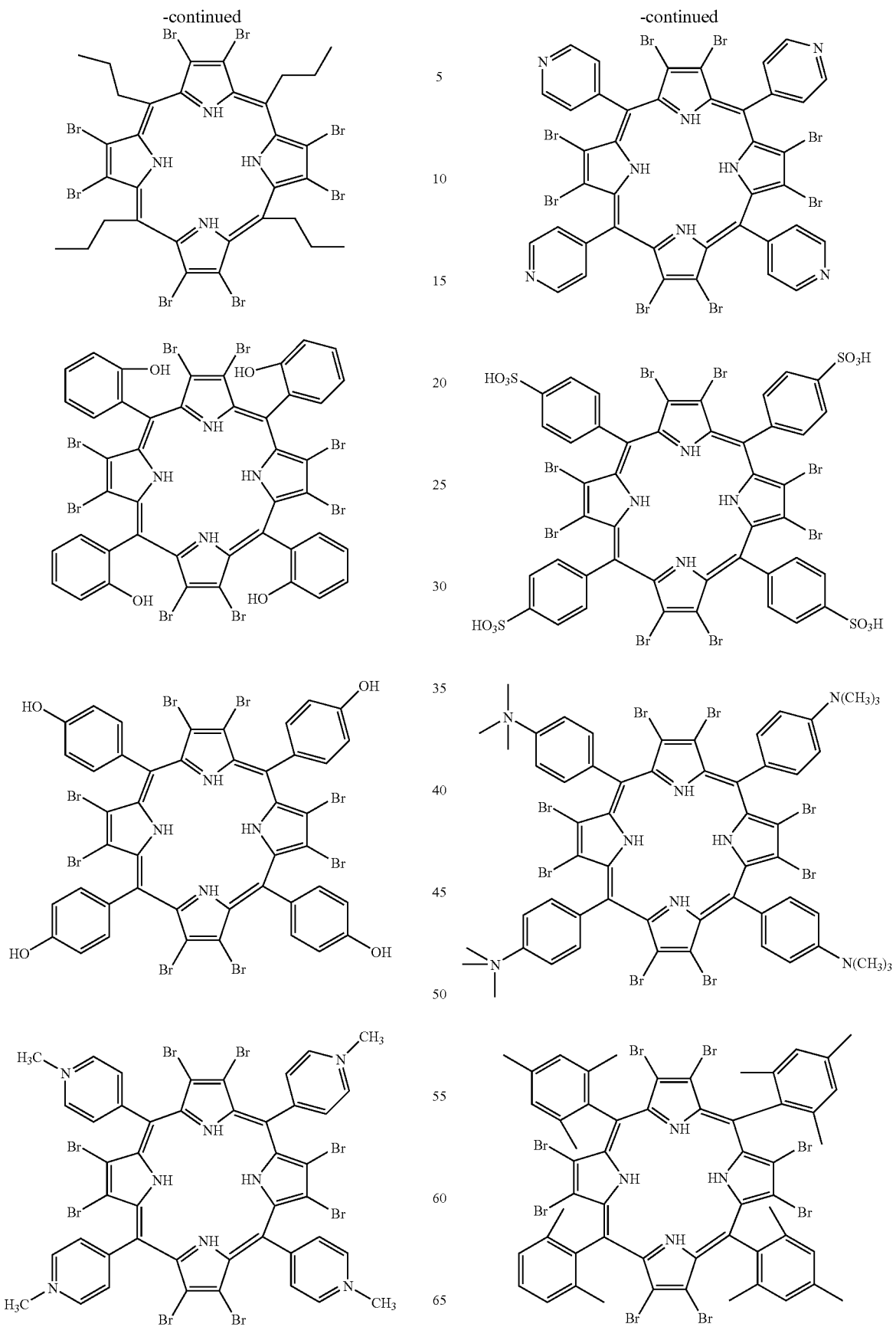

-continued
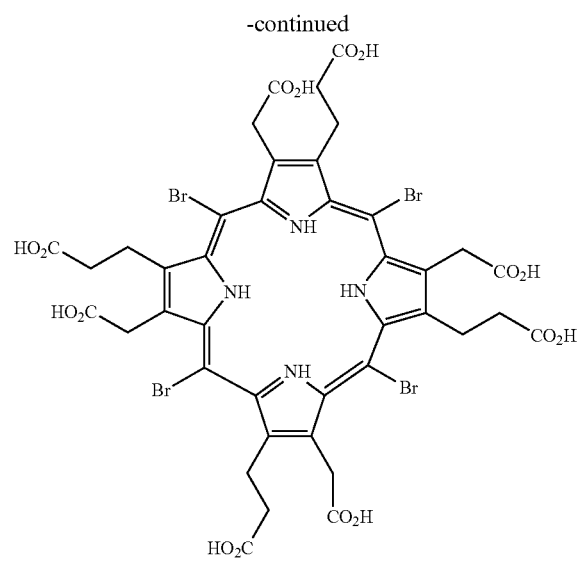
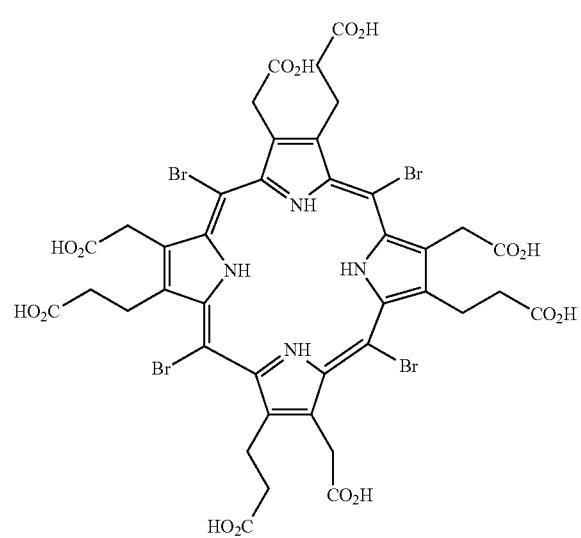
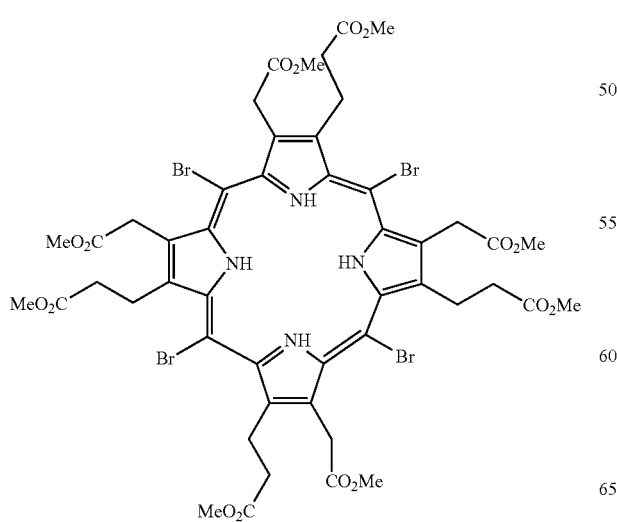
-continued
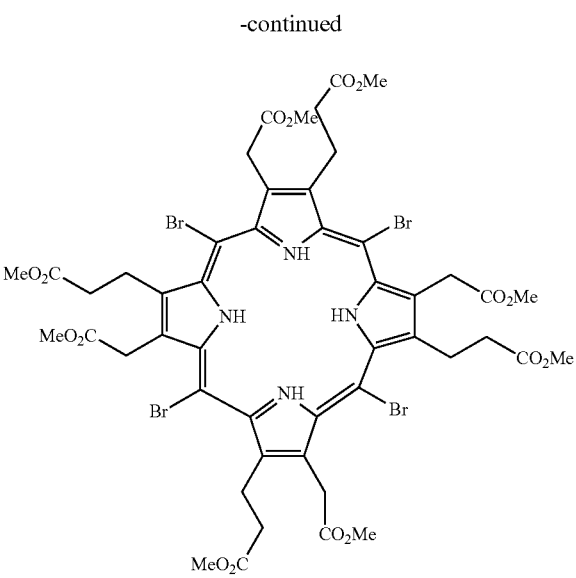
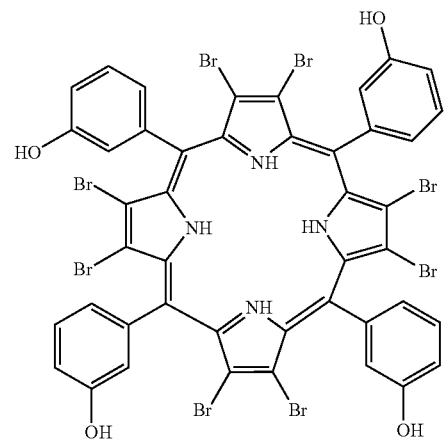
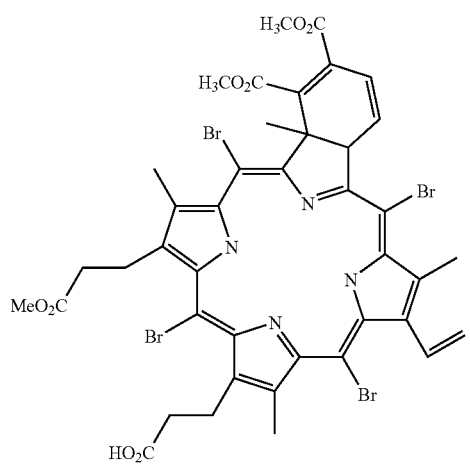

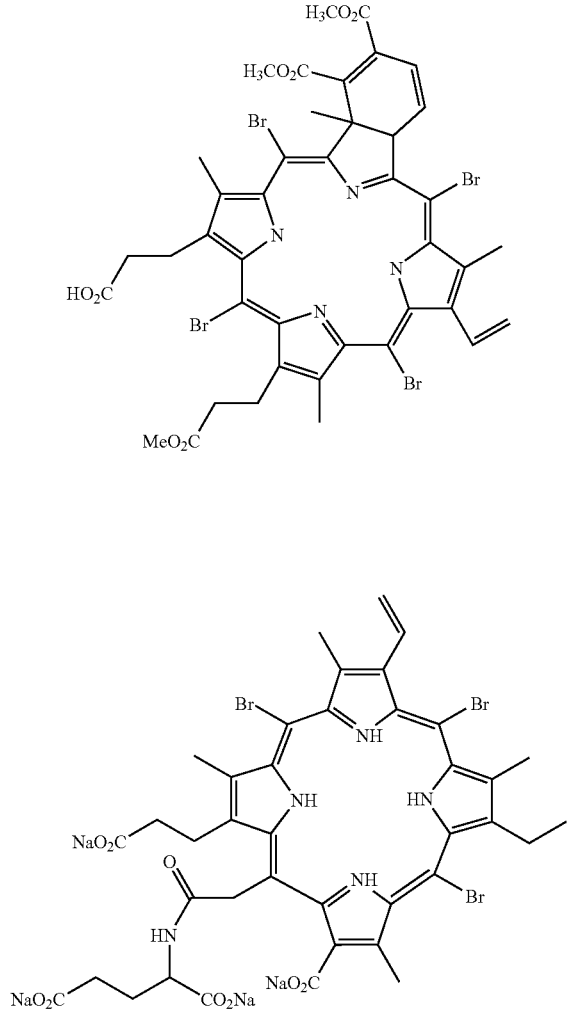
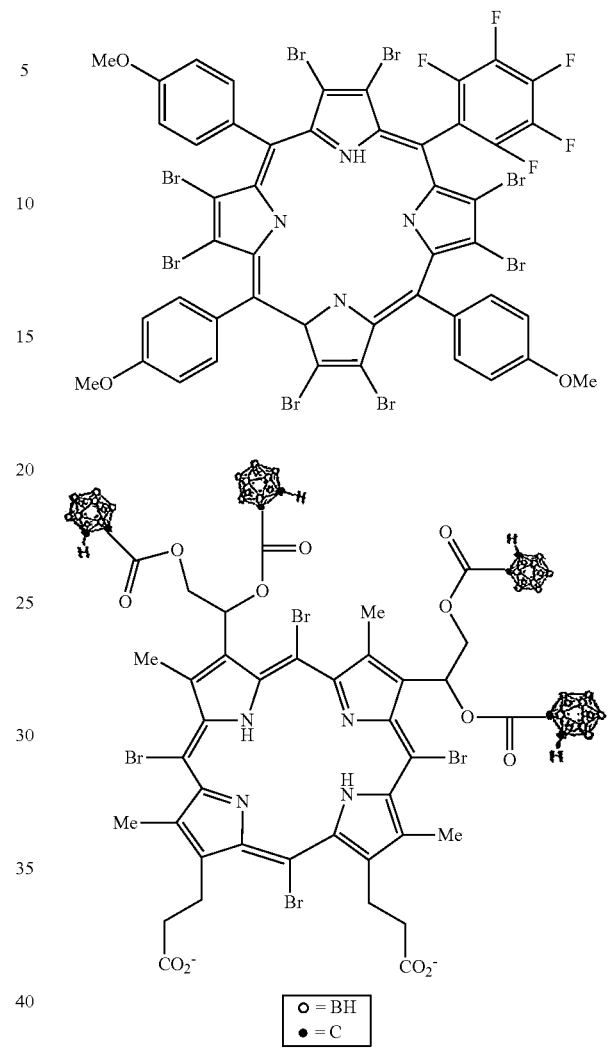
Further preferred compounds of the invention include
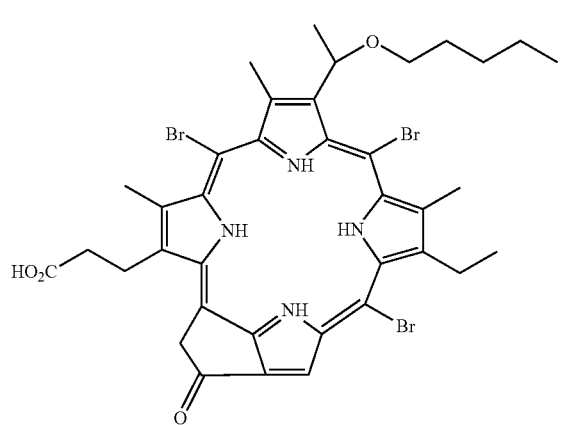
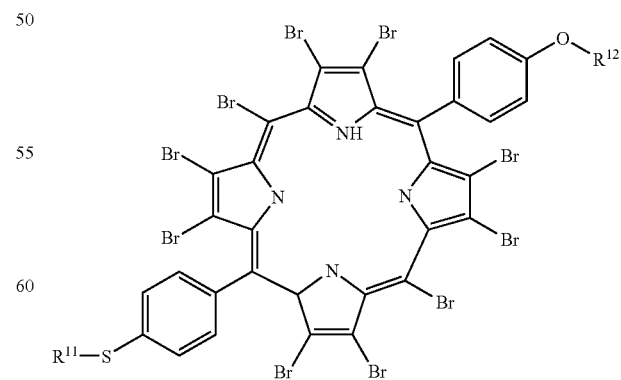
wherein $R^{11}$ is phenyl substituted with $NH_2$ or benzyl and $R^{12}$ is phenyl substituted with $NO_2$ or

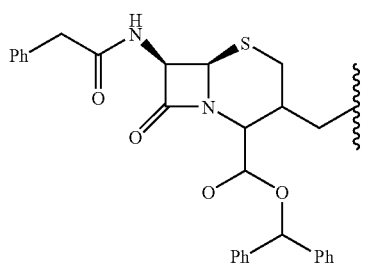
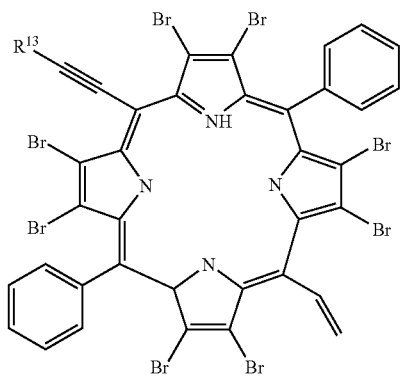
wherein $R^{13}$ is $(CH_2)_3CH_3$, $(CH_2)_5CH_2OH$, or estradiol;
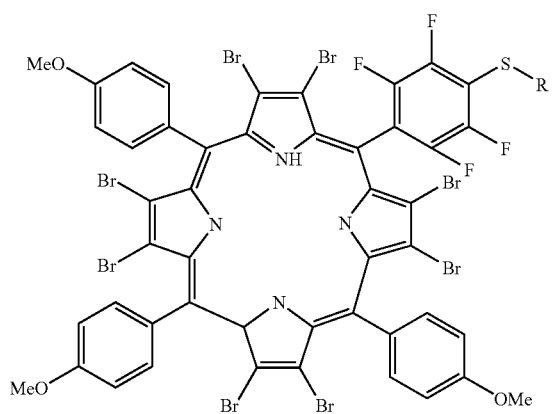
wherein R is phenyl optionally substituted with OH, $NH_2$, MeO or $CO_2Me$; or benzyl, or pyridyl, or $(CH_2)_{17}CH_3$ or hydrogen, or a steroid.
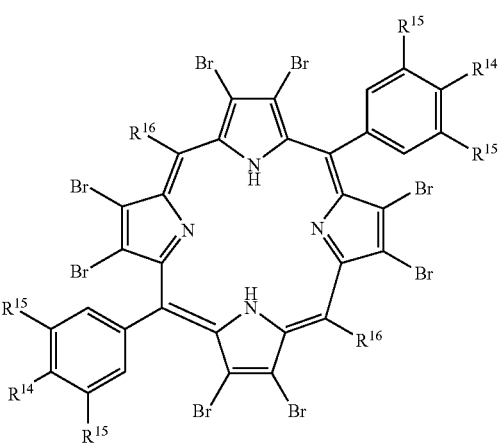
wherein $R^{14}$ is Br, hydrogen, methyl or $N(CH_3)_2$, $R^{15}$ is H or OMe and $R^{16}$ is methyl;
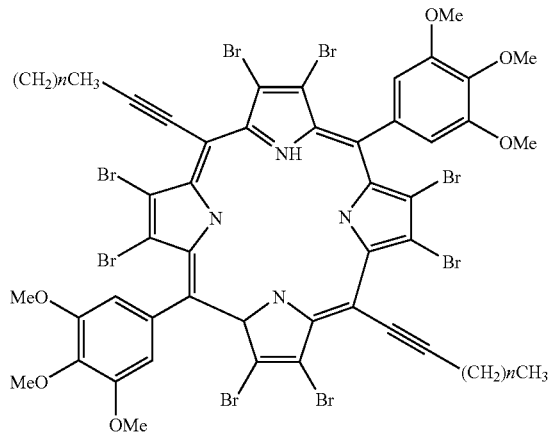
wherein n is 1 to 20, preferably 2 to 15, more preferably 2, 3, 4, 5, 6, 7, 8, 9, 10, 11, 12 or 13;
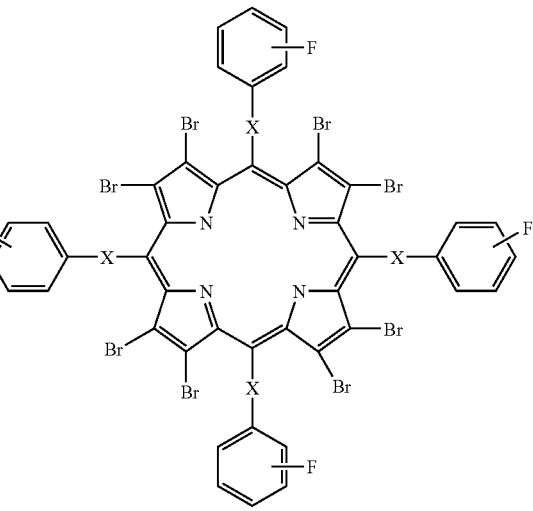
wherein X is $CH_2$, O, $OCH_2$ or absent; or

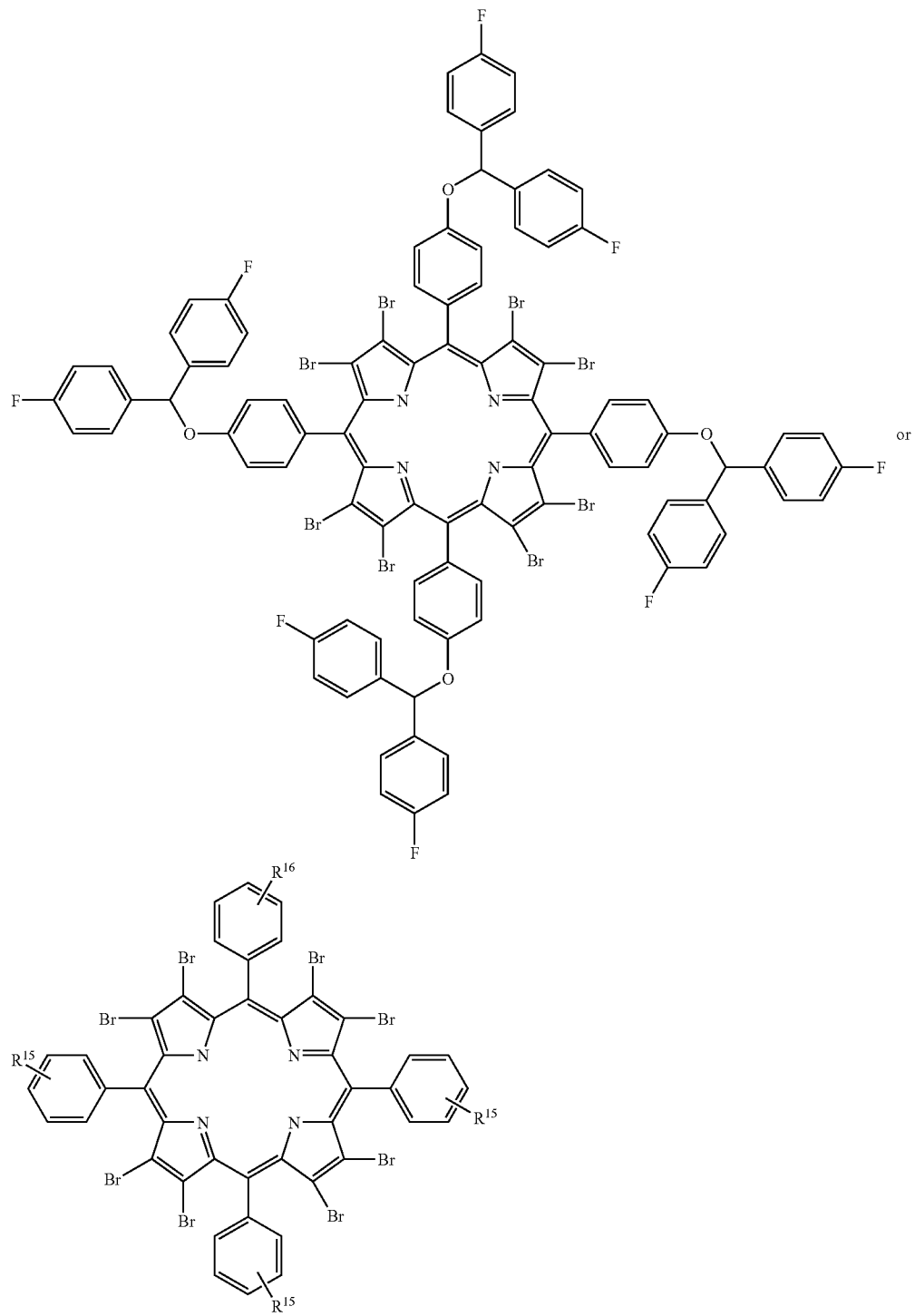

wherein R[15] is 4-(1-methyl-o-carboranylmethyl).

The preferred compounds as illustrated above are also provided in combination with a metal, wherein the metal can be V, Ga, Mn, Fe, Ru, Tc, Cr, Pt, Co, Mi, Cu, Zn, Ge, In, Sn, Y, Au, Ba, W, Gd, Pb, Al or Pt, preferably Au, Zn, Fe, Cr. Sn, Ni, Pt, V, Al, Co, Mn, Cu or Pd.

The third aspect of the invention provides a pharmaceutical composition comprising a compound as defined in the second aspect of the invention and a pharmaceutically acceptable excipient.

The compounds of formula (I) can be formulated according to known methods to produce pharmaceutically useful compositions, whereby the compound of formula (I) is combined in a mixture with a pharmaceutically acceptable carrier.

The resulting composition is pharmaceutically acceptable if it can be tolerated by the recipient. Examples of suitable carriers will be known to persons skilled in the art, and are described in Remingtons' Pharmaceutical Sciences (Maack Publishing Co., Easton Pa.).

The fourth aspect of the invention relates to a compound of formula (I) as defined in the second aspect of the invention for cell ablation by photon activation therapy.

The fifth aspect of the invention provides a process for the production of a compound of formula (I) comprising halogenation of a porphyrin compound. Examples of reagents that can be used to prepare compounds of formula (I) include brominating reagents such as molecular bromine and N-bromosuccinimide (NBS). Chlorinating reagents include N-chlorosuccinimide.

The sixth aspect of the invention provides a method of cell death by photon activation therapy comprising administering a compound of formula (I) as defined in the first aspect of the invention to a subject in need thereof.

The dosage of the compound of formula (I) will vary depending upon factors such as the patient's age, weight, height, sex, medical condition and previous medical history, as well as factors such as the location and severity of condition to be treated, and the degree and rate of deposit of the compound of the invention at the target site, the degree and rate of internalisation of the conjugate, and the rate of clearance of the compound of formula (I).

The dose of the compound of formula (I) administered to a recipient must result in a therapeutically acceptable amount; i.e. its presence must be sufficient to result in cell damage or death upon administration of the X-rays.

The drug dose within the tumour mass needs to be sufficient to generate cell kill. To achieve this the administered dose is in the range of 0.1 mg/kg to 100 mg/kg, preferably 1 mg-50 mg/kg and more preferably 5 mg/kg-25 mg/kg. The compound is ideally homogeneously distributed within the tumour tissue. The compound selectivity tumour: surrounding tissue ratio is in the range of a minimum of 500:1, preferably 100:1 and more preferably 20:1 to 1:1. The amount of compound in the tumour tissue equates to 0.1 micro g/g to 200 micro g/g of compound in the tumour tissue. These easy-to-reduce porphyrins (or porphyrins with electron withdrawing groups) can be used with ionisizing radiation. Ionizing radiation may be beamed in from an external source (e.g. conventional radiotherapy linar accelerators, heavy ion beams such carbon ions, gamma knife, electron beam, proton beams, fast neutron beams) or applied internally within the tissue mass by way of conventional radioactive seeds such as Iridium-192 seeds, Palladium-103 seeds or Iodine-125 seeds Radium-226, Caesium-137, Cobalt-60, Gold-198, Strontium-90, Yttrium-90 (Brachytherapy).

The compound of the invention can be used with proton therapy, proton therapy, antiporton therapy, pion therapy, radio-immunotherapy, electron beam therapy as well as conventional radiotherapy.

The drug substance can be administered to the patient prior to the administration of irradiation. Normally the drug may be given in the range of 10-180 minutes to 48-96 hours before the radiation is administered. The drug can be given daily or at regular or non-regular intervals such interval being from 5 to 21 days preferably from 7 to 10 days so as to maintain a therapeutically effective amount within the tumour mass. For example, conventional radiotherapy dose is administered every day, 5 days per week for 4 to 6 weeks. The compounds can also be used in the variant of conventional radiotherapy known as Continuous Hyper Accelerated Radiotherapy (CHART). For example approximately 39 radiation fractions of 1.2 Gy-1.5 Gy can be delivered over a space of 11 days. The compounds can also be used with Intensity Modulated Radiotherapy (IMRT). IMRT is a technique that delivered x-rays precisely to its target with a varying radiation dose over a given area.

For the purpose of this invention; the mode of drug administration is ultravenous, oral, intraperitaneal, mucosal, dermal, vaginal or oral.

The useful total dose of x-rays for the purposes of this invention is approximately 0.1 Gy to 200 Gy, preferably 1 Gy to 120 Gy, more preferably 15 Gy to 100 Gy. The fractionated X-ray dose is 0.1 to 10 Gy, preferably 0.5 Gy to 3 Gy, more preferably, 0.5 Gy to 2 Gy. The total number fraction are 1 to 100, preferably 1 to 70, more preferably 1 to 40. The radiation is administered for 1 to 100 days, preferably 1 to 70 days, more preferably 1 to 40 days.

The compounds are particularly useful for Conventional radiotherapy, accelerated hyperfractionated radiotherapy and intensity modulated radiotherapy.

The preferred ionization source is x-rays. The useful x-ray for the purposes of this invention have an energy of approximately 10 kiloelectron volts to 1000 megaelectron volts, the preferred range is 100 keloelectron volts to 50 megaelectron volts and more preferred range is 1 megaelectron volts to 20 megaelectron volts.

The present invention will now be illustrated by reference to one or more of the following non-limiting examples.

EXAMPLES

Bromination of 5,10,15,20-tetraphenyl-21H,23H-porphine

A solution of bromine (1.55 ml, 30 mmol) in $CCl_4$ (20 ml) was added dropwise, over 20 min to a stirred solution of 5,10,15,20-tetraphenyl-21H,23H-porphine (600 mg, 0.976 mmol) in $CCl_4$ (80 ml) and the resulting mixture stirred for 1 h. The mixture was diluted with dichloromethane (100 ml) and washed with 10% aqueous sodium metabisulfite (100 ml). The organic layer was collected, washed with brine, dried (MgSO4)) and the solvents evaporated.

Inhibited Cell Proliferation:

The compounds are used as a pre-treatment in in vitro cell culture using animal and human tumour cell lines cultures (human breast tumour cell lines (MCF-7, ZR-75-1), the mouse androgen-responsive Shionogi breast carcinoma (SC115) cell line, human colon tumour cell lines HT29 and SW480) to conduct suppression of cell proliferation. Dark toxicity and X-Ray+drug compound indicate that the halogenated compounds are activated and significantly reduce cell proliferation as measured by standard $IC_{50}$ scores. Titrations studies provide an indication of the dose of drug required for use in the x-ray+drug studies. Single dose and fractionated dose of x-ray radiation are used equating to typically 25 Gy, 35 Gy, 45 Gy which is equivalent to 50-70 Gy fractionated. Fractionated dose studies are conducted at 1-2 Gy factions over 2-5 days. The reduction in proliferation is 100% to 10%, typically 85%-95% inhibition can be observed.

Experimental evaluation of therapeutic efficacy entail localised irradiation of tumour-bearing animals in the presence of the halogenated compound. The administration protocols and the timing after administration at which irradiation begins are determined by prior pharmacokinetic and biodistribution studies. The assessment consist of quantification of changes in tumour volume, incidence of tumour ablation and long-term survival. By way of comparison, and to enable calculation of RBE/CBE factors, graded doses of x-rays and of the thermal beam alone is given.

In vivo studies: These are conducted in standard rodent tumour models using for example human xenograft tumours glioma U343, prostate adenocarcinoma pc-3, head and neck squamous carcinoma-pharynx htb-43 fadu, breast carcinoma htb-19, estrogen independent metatstatic breast carcinoma, human colon carcinoma t-84, lung squamous cell carcinoma mri-h-165.

The mouse mammary sarcoma EMT6 tumour model in Balb/c mice weighing 16-22 g is used to demonstrate biodistribution and compound activity. The tumours can reach a diameter of 7-9 mm. The compound is administered iv or ip in for example 5% cremophore EL or 3% Ethanol and 3% PEG 800 solution or 5% cremophore EL and 3% ethanol in saline. Drug concentrations of 50-100 mg/ml are used. Tumours may receive single or multiple irradiations which are commenced 2 hrs, 12 hrs, 24 and 48 hrs after drug administration. An average dose rate is 100-200 cGy per minute. The tumour size is measured prior to and after irradiation. Single faction of 25, 35 and 45 Gy dose are used.

Standard histopathological analysis is carried out on irradiated normal tissues and tumours using standard techniques. Animals are perfusion-fixed using 10% buffered formal saline.

Dose-response data using the various endpoints is assessed using probit analysis, and ED50 and TCP50 values are derived from the fitted curves. These values are used to calculate RBE/CBE factor values. Appropriate control groups are used in all studies. In therapy experiments, the percentage survival versus time following irradiation is analysed using the Kaplan-Meier method. The survival times in each of the experimental groups is ordered and ranked for comparison by a non-parametric statistical technique, Wilcoxin 2-Sample Test Outcome: The above experiments show compounds of the invention accumulate in the tumour mass and are eliminated from the blood over a period of 1-2 days. Post irradiation x-ray alone generate approximately 30% tumour free whilst treatment with the halogenated compound+X-ray irradiation generates 40% to >90% tumour free after 40-100 days. The number of tumour free and or level of tumour control is a function of compound potency and x-ray dose used.

Patient Treatment: The compound is used to pre treatment for all patients undergoing radiotherapy. The patient is given the drug substance prior to a course of radiotherapy (Conventional Radiotherapy or CHART or IMRT) and toped up as and when required until the radiotherapy course has been completed. Conventional radiotherapy will deliver a x-ray dose of 50 Gy-60 Gy over a period of 4-6 weeks, 5 days per week, in approximate fractions of 2 Gy using standard 4-10 Megaelectronvolt radiotherapy linear accelerators. If CAHRT is used then the course of radiotherapy is continuous for 11 days delivering a total dose of 50-60 Gy in fractions of 1.2-1.5 Gy with an average of 3.5 fractions per day every day for the duration of the treatment. The outcome of using the above drug compounds is to significantly enhance the therapeutic outcome. This is in the region of 20-80% or more improvement over the radiotherapy alone treatment.

BRIEF DESCRIPTION OF THE DRAWING

FIG. 1 illustrates the effect of administration of the compound of the invention in terms of % tumour free.

The invention claimed is:
1. A method of causing cell death by photon activation therapy comprising administering a compound of formula (I) to a subject in need thereof and then treating the subject with X-ray radiation that activates the compound, wherein the photon activation therapy is used to treat cancer,

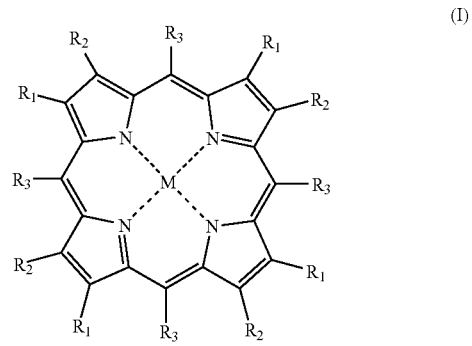

(I)

wherein each $R^1$ is independently selected from hydrogen, optionally substituted $C_{1-8}$ alkyl, optionally substituted $C_{2-8}$ alkenyl, halide, $SO_3R^4$, or $NO_2$, wherein the substituents are selected from one or more of $C_{1-6}$ alkyl, $R^5$, =O, $OR^5$, $CO_2R^5$, $CONR^6R^6$, and each substituent may further be substituted with one or more of $CO_2R^5$ or $OR^5$;

wherein each $R^2$ is independently selected from hydrogen, optionally substituted $C_{1-8}$ alkyl, optionally substituted $C_{2-8}$ alkenyl, halide, $SO_3R^4$, $NO_2$, wherein the substituents are selected from one or more of $C_{1-6}$ alkyl, $R^5$, =O, $OR^5$, $CO_2R^5$, $CONR^6R^6$, and each substituent may further be substituted with one or more of $CO_2R^5$ or $OR^5$;

wherein $R^1$ and $R^2$ may together form a six membered ring, wherein said ring can be fully saturated, partially saturated or unsaturated and is optionally substituted with one or more of =O, halide, $SO_3R^4$, $NO_2$, $C_{1-6}$ alkyl or $CO_2R^5$;

wherein each $R^3$ is independently hydrogen, halide, $C_{1-20}$ alkyl, $C_{2-20}$ alkenyl, $C_{2-20}$ alkynyl, $C_{1-6}$ haloalkyl, $C_{3-12}$ aryl or $C_{3-12}$ heteroaryl, $C_{1-20}$ alkyloxy, $C_{2-20}$ alkenyloxy, $C_{2-20}$ alkynyloxy, $C_{3-12}$ aryloxy, $C_{3-12}$ heteroaryloxy; wherein the alkyl, alkoxy, alkenyl, alkenyloxy, alkynyl, alkynyloxy, aryl, aryloxy, heteroaryl and heteroaryloxy group are optionally substituted with one or more of $C_{1-6}$ alkyl, aryl, $R^5$, $OR^5$, $NR^6_2$, $SO_3R^4$, $NO_2$, halide, $CO_2R^5$ or $B(OR^6)_2$ and each substituent may be further substituted with one or more of halide, $C_{1-6}$ alkyl;

wherein $R^2$ and $R^3$, or $R^1$ and $R^3$ may together form a five membered ring, wherein said ring can be fully saturated, partially saturated or unsaturated and is optionally substituted with one or more of =O, $C_{1-8}$ alkyl, or $CO_2R^5$;

wherein $R^4$ is hydrogen or $C_{1-6}$ alkyl; $R^5$ is hydrogen or $C_{1-6}$ alkyl, $C_{6-12}$ aryl, a biocompatible polymer or a counter ion, said alkyl or aryl groups being optionally substituted with $NR^6_2$, $NO_2$, $C_{1-4}$ alkyl or $C_{6-12}$ aryl; $R^6$ is hydrogen or $C_{1-6}$ alkyl, $R^7$ is hydrogen or $C_{1-6}$ alkyl optionally substituted with $CO_2R^5$;

and M is a metal or hydrogen;

and wherein one or more occurrence of $R^1$, $R^2$ or $R^3$ is an electron withdrawing group selected from F, Cl, Br or I.

2. The method as claimed in claim 1 wherein one or more of the $R^1$ groups is F, Cl, Br or I.

3. The method as claimed in claim 1 wherein one or more of the $R^2$ groups is F, Cl, Br or I.

4. The method as claimed in claim 1 wherein one or more of the $R^3$ groups is F, Cl, Br or I.

5. The method as claimed in claim 1 wherein the cancer is a solid tumour and/or metastasis.

6. The method as claimed in claim 1 wherein the cancer is a lymphoma, skin cancer, lung cancer, head and/or neck cancer, bone cancer, prostate cancer, colon cancer, cervical cancer breast cancer, brain cancer, liver cancer or pancreatic cancer.

7. The method as claimed in claim 6 wherein the skin cancer is malignant melanoma, including squamous cell carcinoma, merkel cell carcinoma, or basal cell carcinoma.

8. The method as claimed in claim 1 wherein the subject is a mammal.

9. The method as claimed in claim 1, wherein the compound of formula (I) comprises a structure selected from the group consisting of:

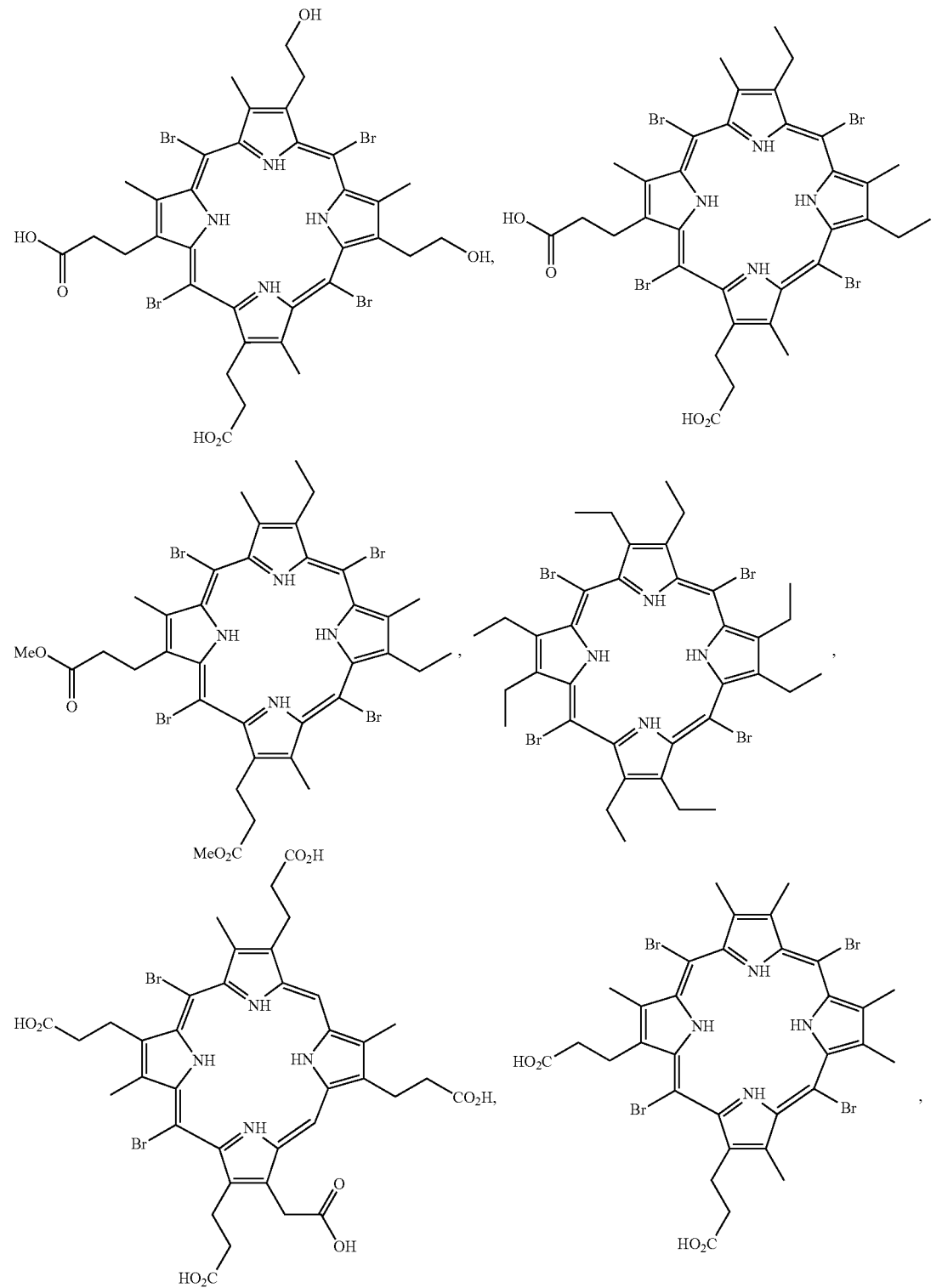

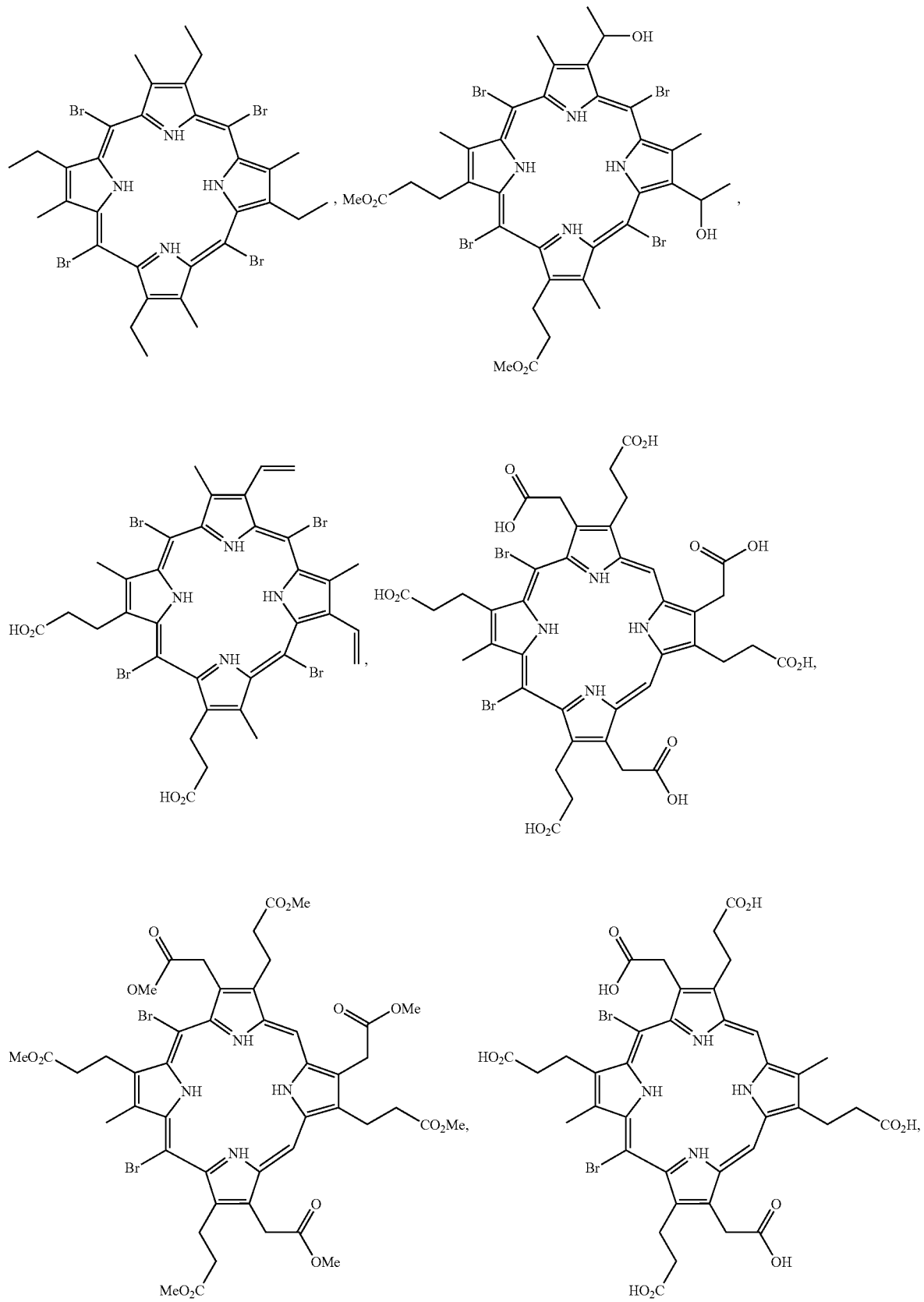

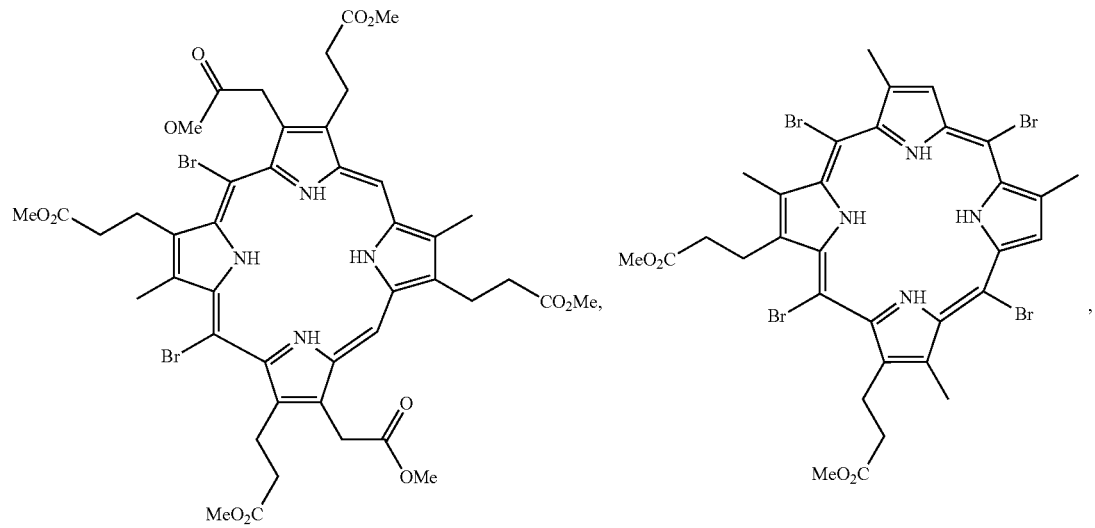
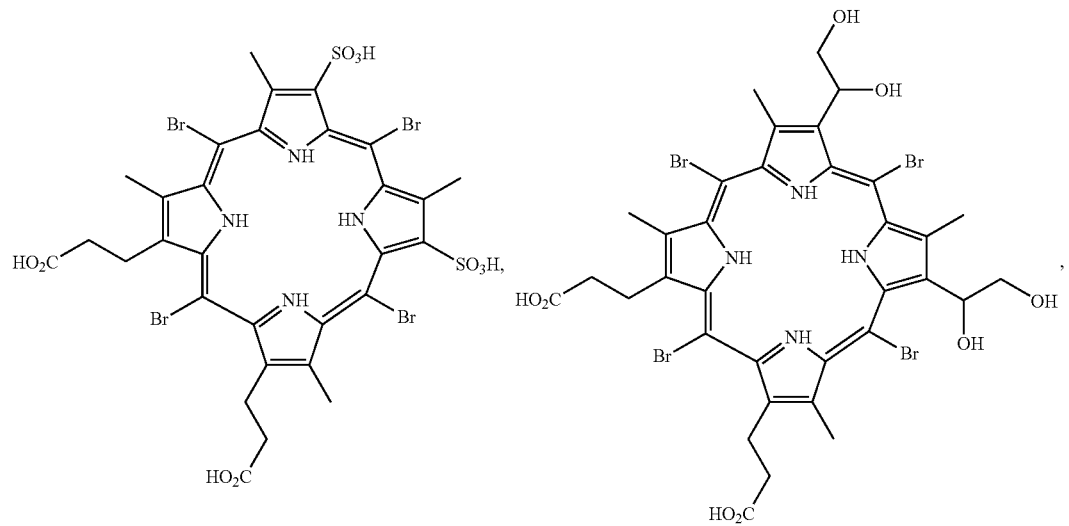
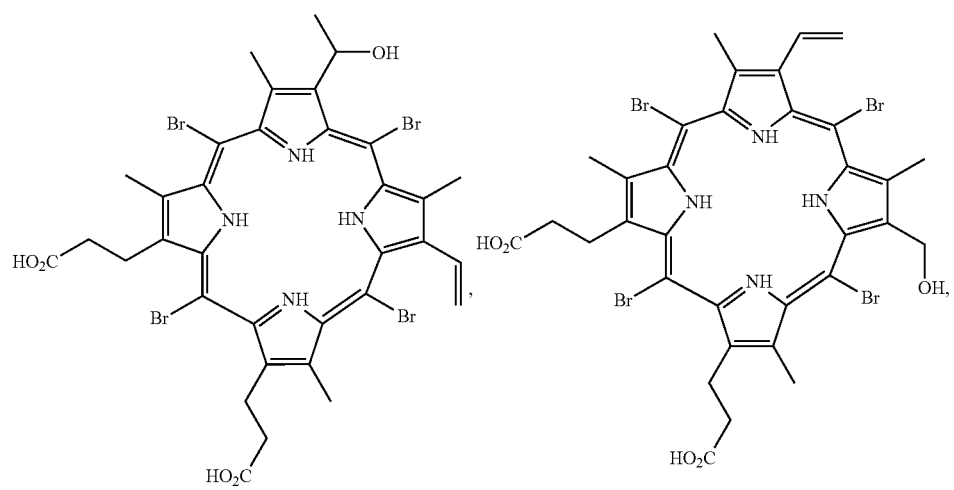

-continued
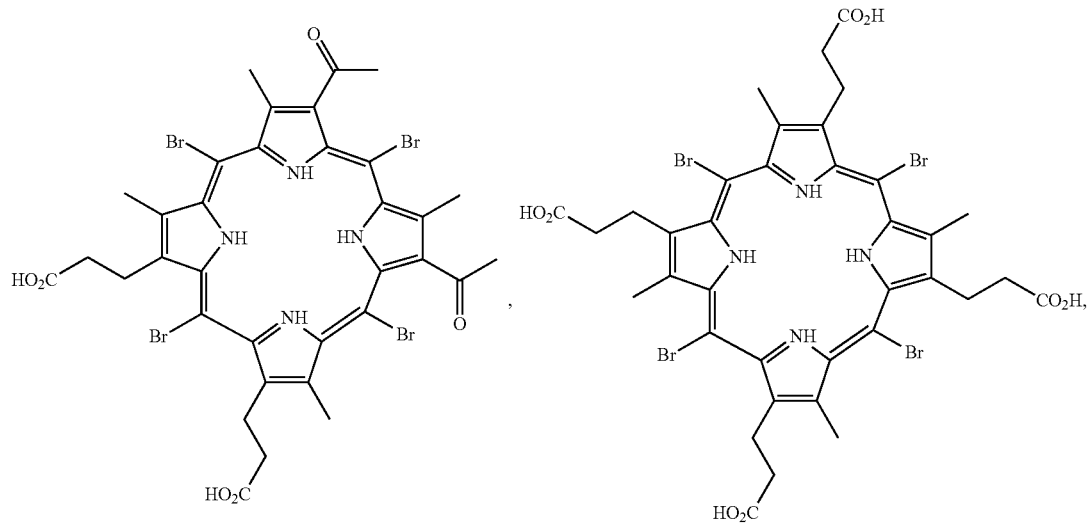
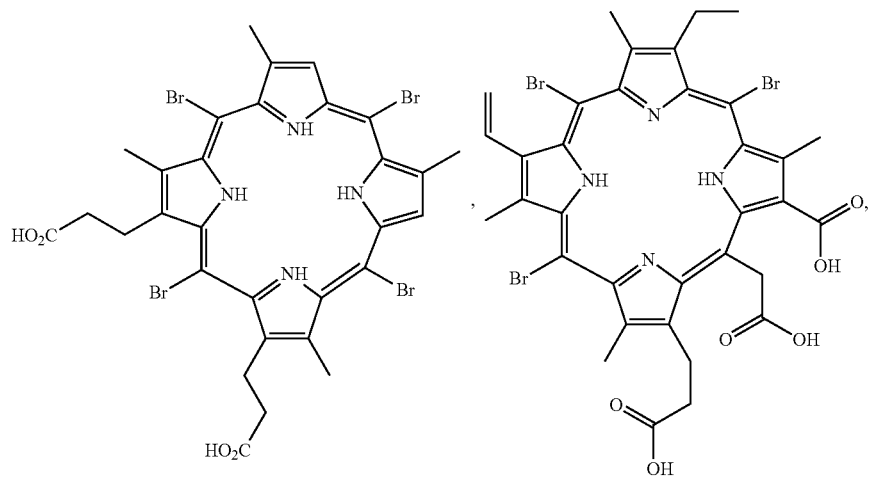
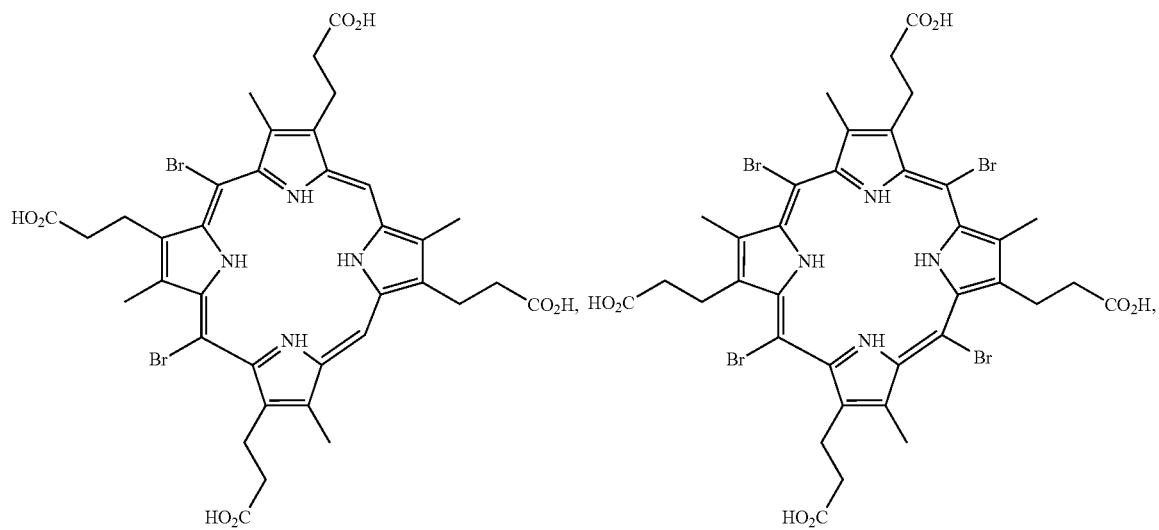

-continued
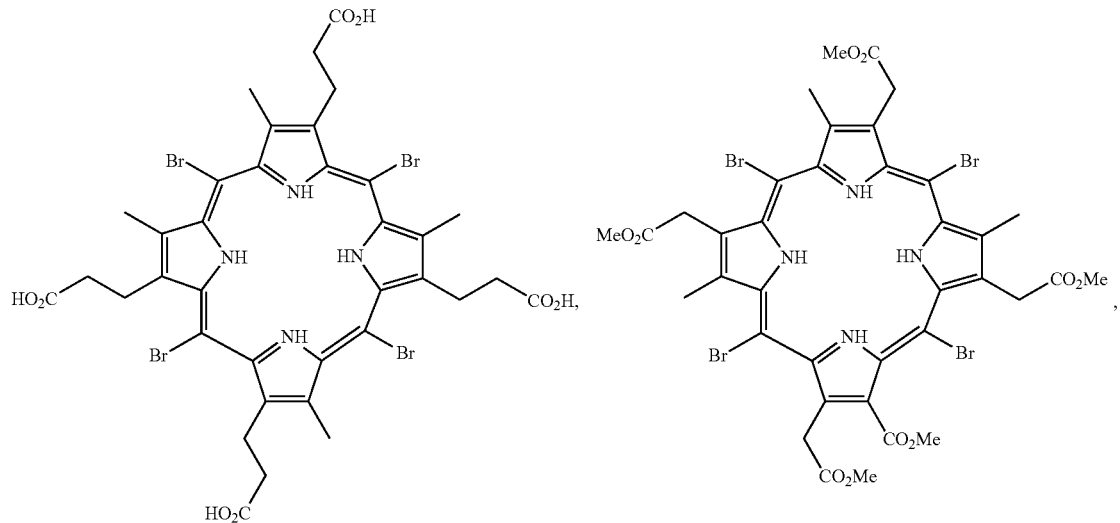
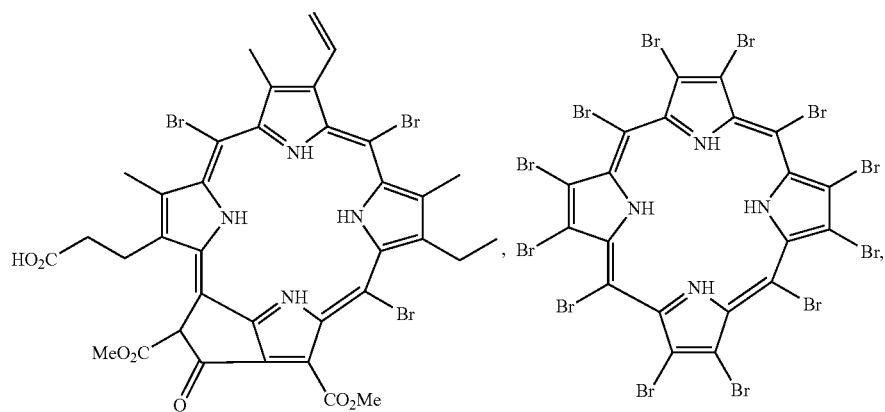
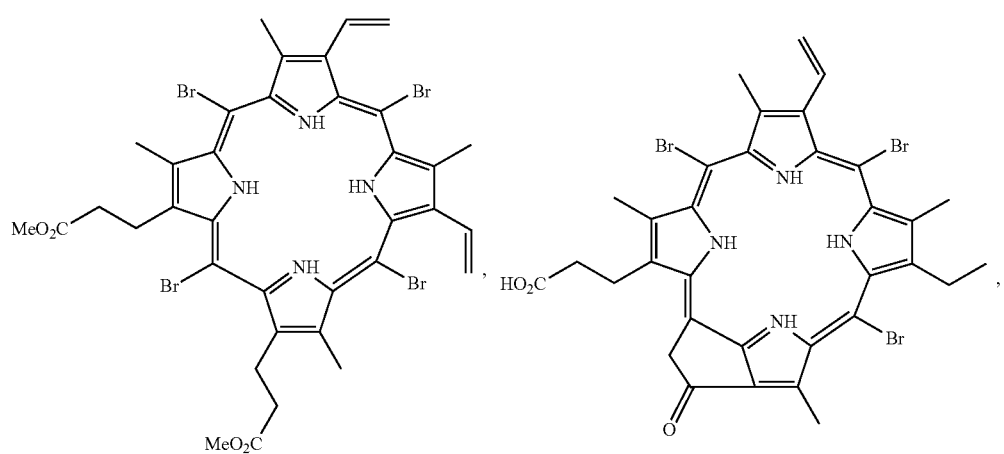

-continued
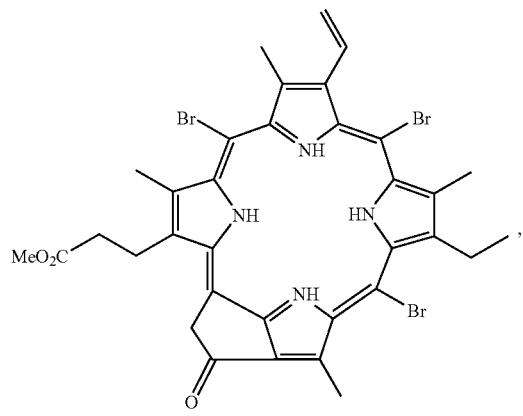 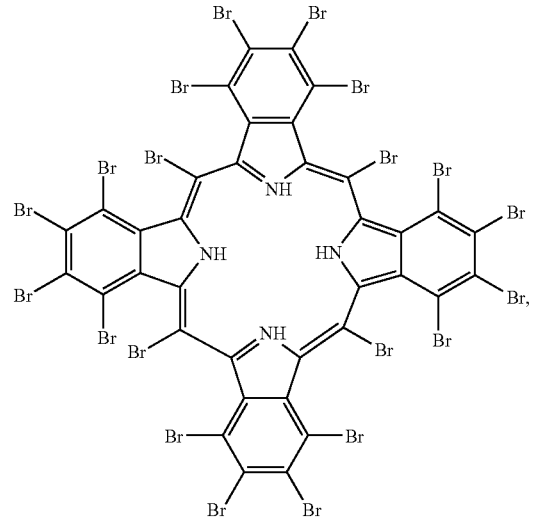
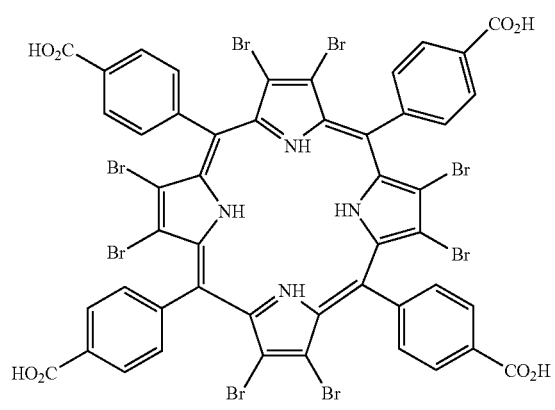 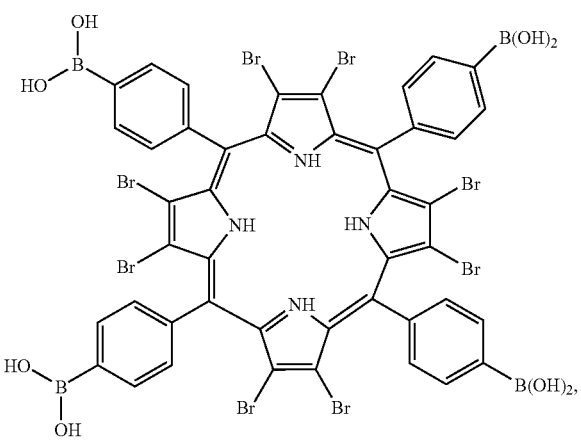
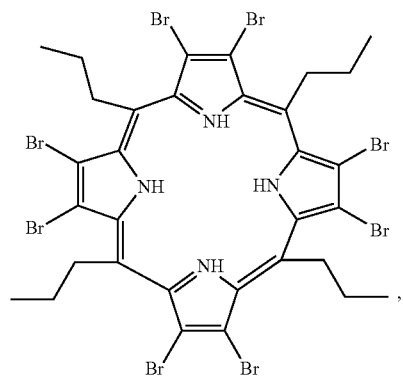 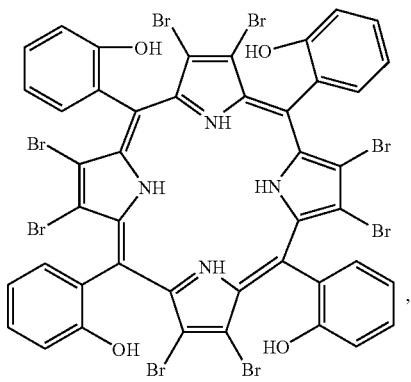

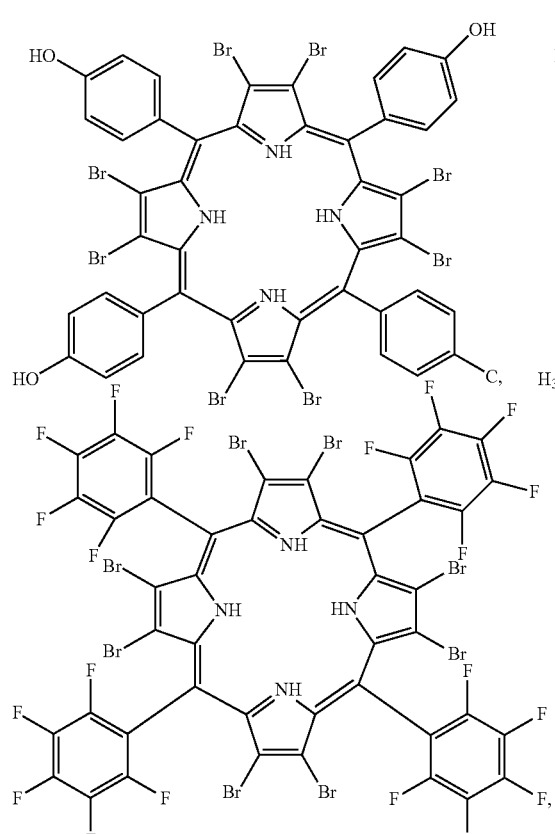
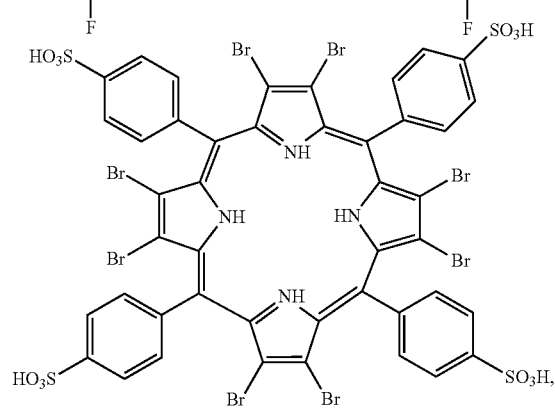
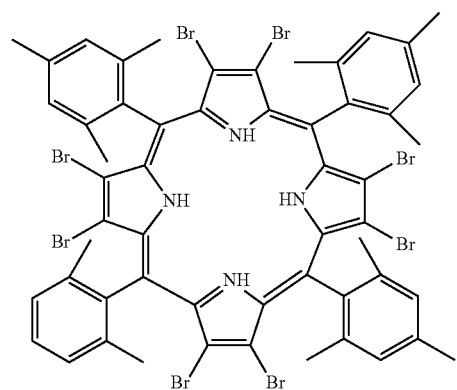
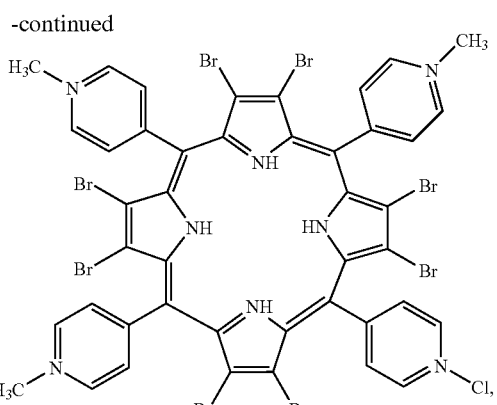
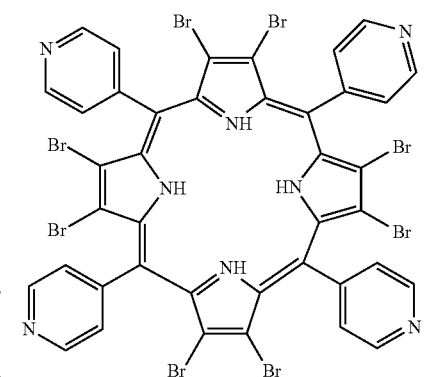
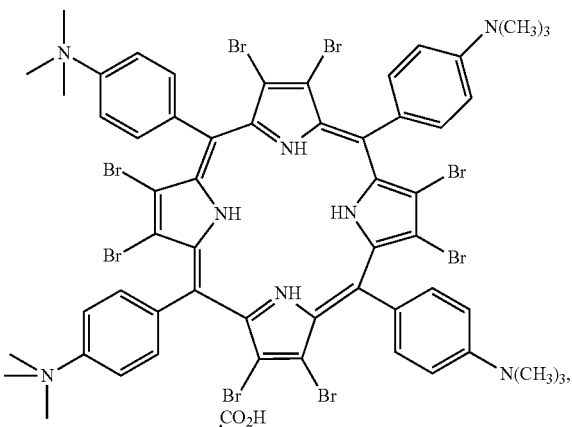
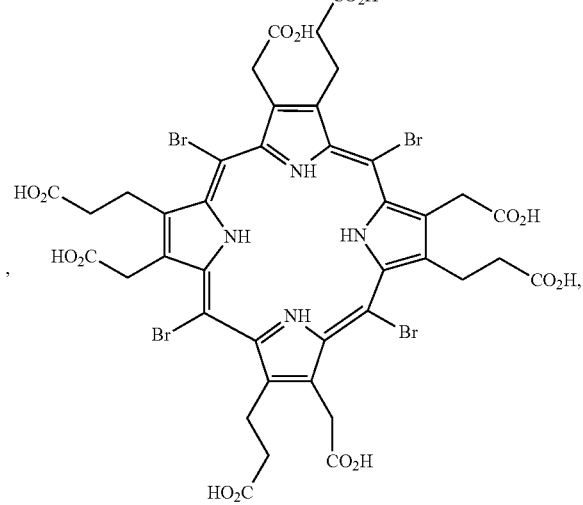

-continued
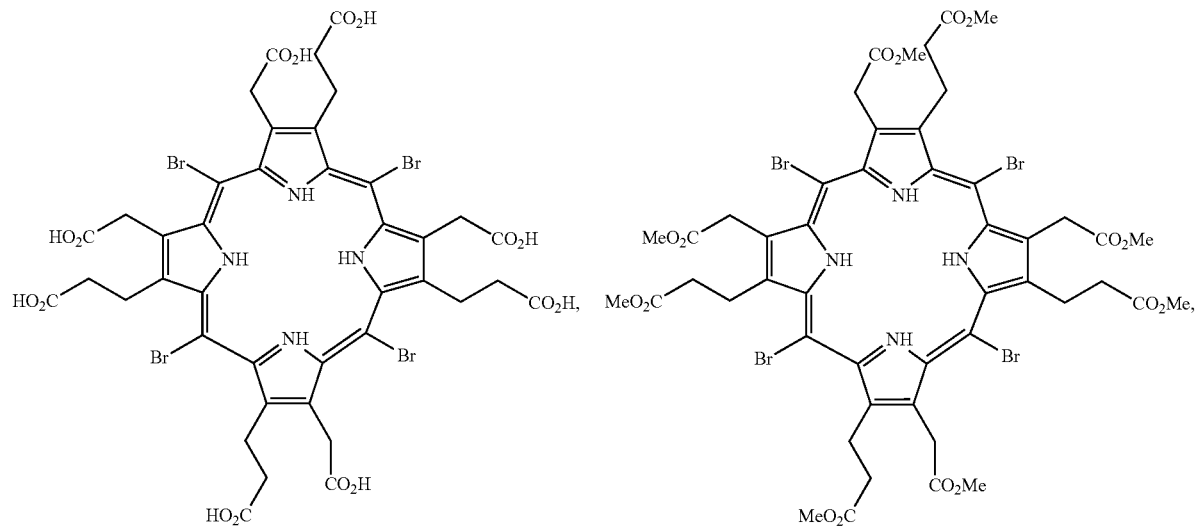
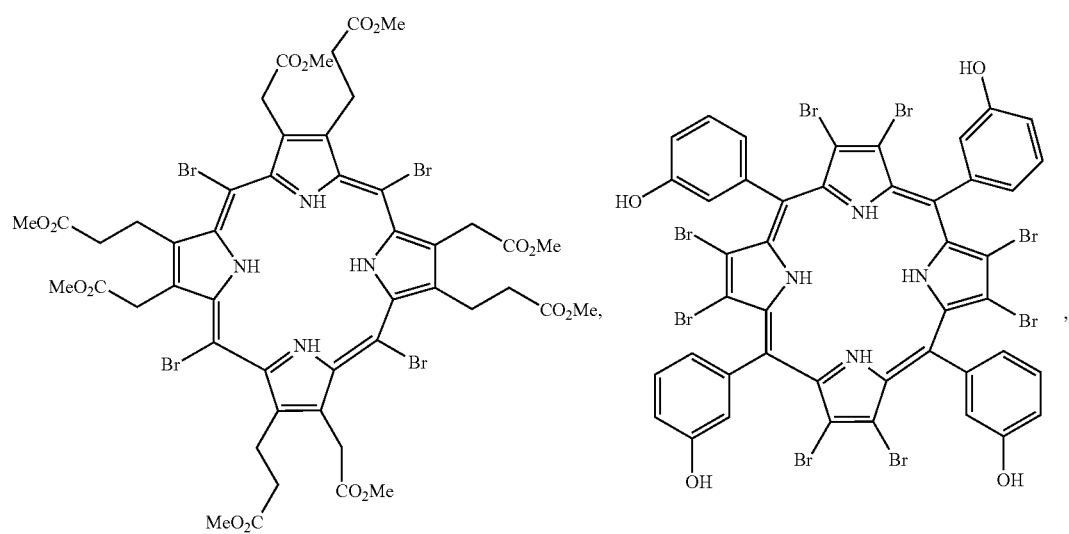
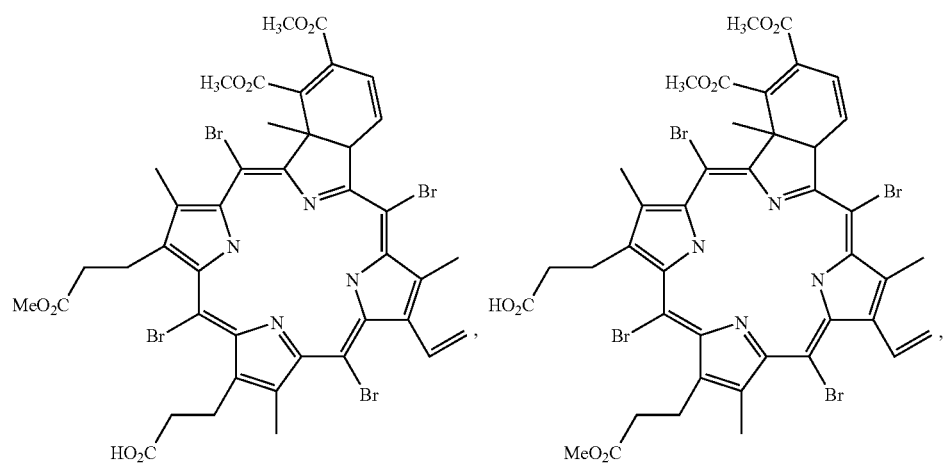

-continued
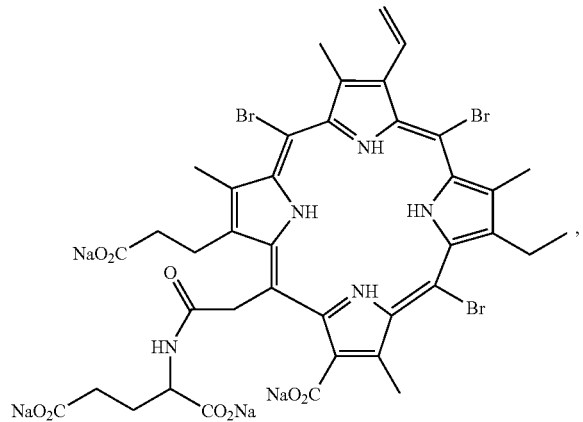
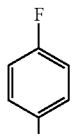
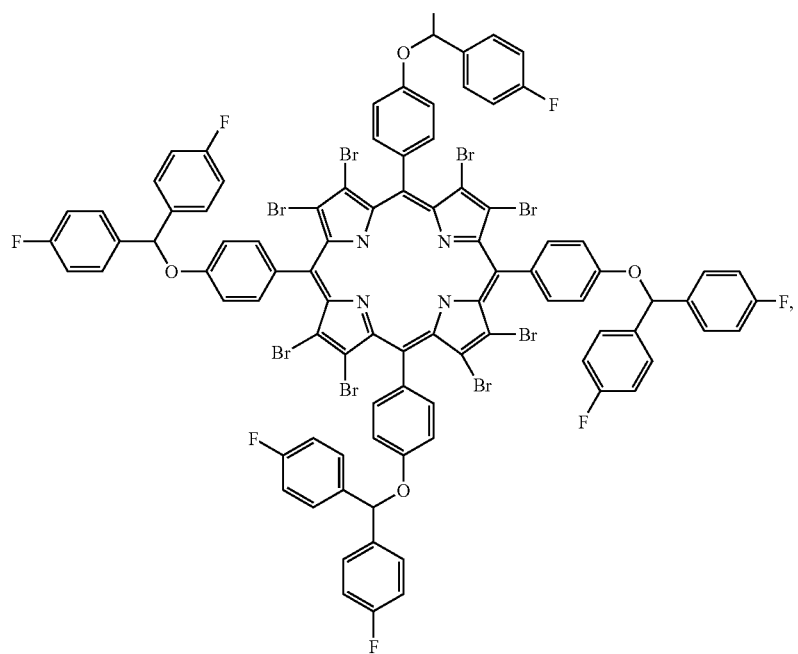
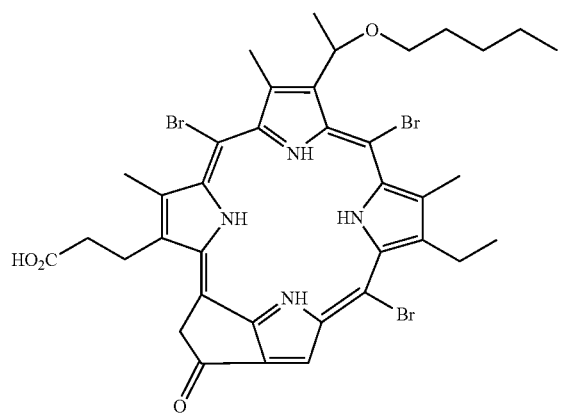
, and

-continued

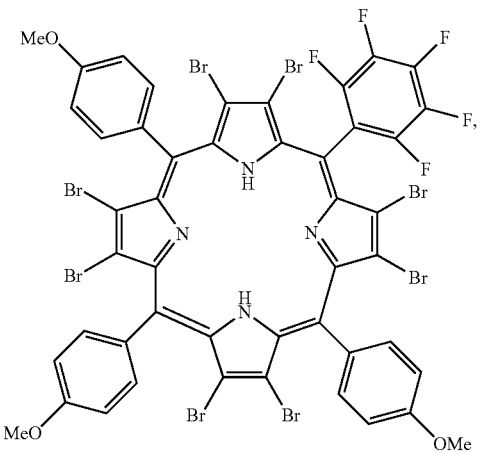

together with M co-ordinated to the porphyrin structure as illustrated in claim 1, wherein M is a metal or hydrogen.

10. A method of causing cell death by photon activation therapy comprising administering to a subject in need thereof a compound which comprises the structure:

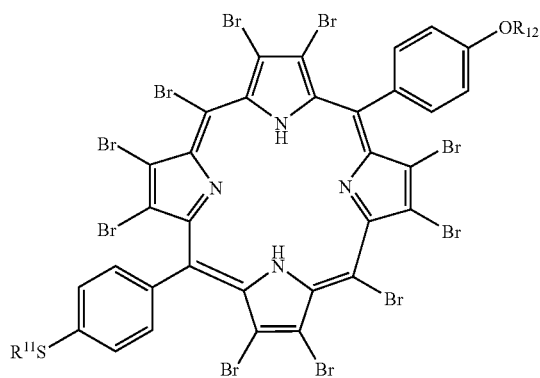

wherein $R^{11}$ is phenyl substituted with $NH_2$ or benzyl and $R^{12}$ is phenyl substituted with $NO_2$ or

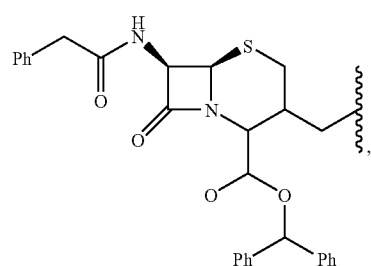

together with M co-ordinated to the porphyrin structure as illustrated in claim 1, wherein M is a metal or hydrogen;

or a compound which comprises the structure:

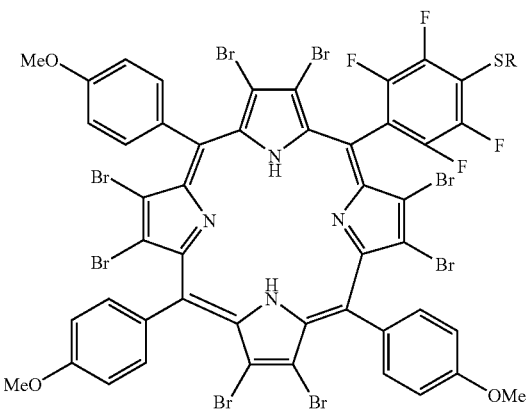

wherein R is $(CH_2)_{17}CH_3$, hydrogen, a steroid, benzyl, pyridyl, or phenyl optionally substituted with OH, $NH_2$, MeO or $CO_2Me$, together with M co-ordinated to the porphyrin structure as illustrated in claim 1, wherein M is a metal or hydrogen; and then treating the subject with X-ray radiation that activates the compound, wherein the photon activation therapy is used to treat cancer.

11. The method as claimed in claim 1, wherein the compound of formula (I) comprises the structure:

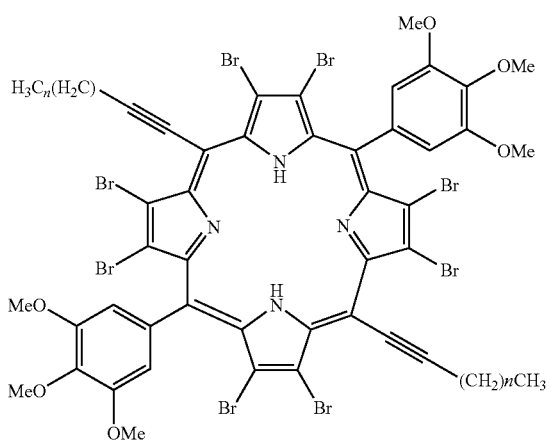

wherein n is 1 to 20, together with M co-ordinated to the porphyrin structure as illustrated in claim 1, wherein M is a metal or hydrogen.

12. The method as claimed in claim 1, wherein the compound of formula (I) comprises the structure:

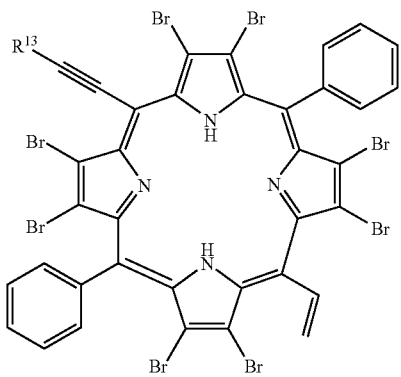

wherein $R^{13}$ is $(CH_2)_5CH_3$, $(CH_2)_5CH_2OH$, or estradiol, together with M co-ordinated to the porphyrin structure as illustrated in claim 1, wherein M is a metal or hydrogen.

13. The method as claimed in claim 1, wherein the compound of formula (I) comprises the structure:

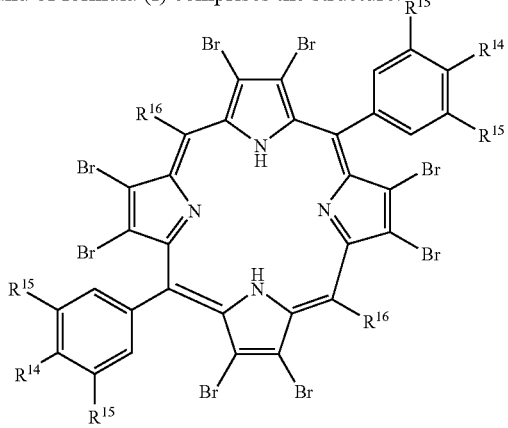

wherein $R^{14}$ is Br, hydrogen, methyl or $N(CH_3)_2$, $R^{15}$ is H or OMe and $R^{16}$ is methyl, together with M co-ordinated to the porphyrin structure as illustrated in claim 1, wherein M is a metal or hydrogen.

14. The method as claimed in claim 1, wherein the compound of formula (I) comprises the structure:

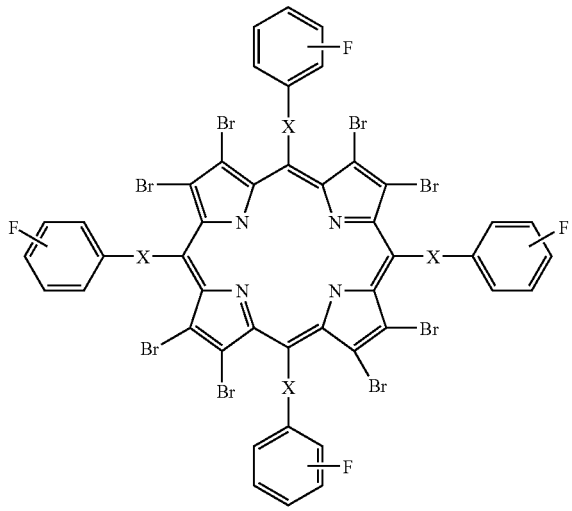

wherein X is $CH_2$, O, $OCH_2$ or absent, together with M co-ordinated to the porphyrin structure as illustrated in claim 1, wherein M is a metal or hydrogen.

15. The method as claimed in any one of claims 9, 10 or 11 to 14, wherein M is a metal selected from the group consisting of V, Mn, Fe, Ru, Tc, Cr, Pt, Co, Ni, Cu, Zn, Ge, In, Sn, Y, Au, Ba, W, Gd, Ga, Pb, Al and Pd.

16. The method as claimed in any one of claims 9, 10 or 11 to 14, wherein a pharmaceutical composition comprising the compound and a pharmaceutically acceptable excipient is administered to the subject.

17. The method as claimed in claim 1, wherein M is a metal selected from the group consisting of V, Mn, Fe, Ru, Tc, Cr, Pt, Co, Ni, Cu, Zn, Ge, In, Sn, Y, Au, Ba, W, Gd, Ga, Pb, Al and Pd.

18. The method as claimed in claim 1, wherein M is a metal selected from the group consisting of Au, Zn, Fe, Cr, Sn, Ni, Pt, V, Al, Co, Mn, Cu and Pd.

19. The method as claimed in claim 1, wherein one or more of $R^1$, $R^2$ or $R^3$ is Br.

20. The method as claimed in claim 1, wherein $R^5$ is Na or K.

21. The method as claimed in claim 1, wherein the compound of formula (I) is brominated 5,10,15,20-tetraphenyl-21H, 23H porphine, wherein M is hydrogen or a metal selected from the group consisting of V, Mn, Fe, Ru, Tc, Cr, Pt, Co, Ni, Cu, Zn, Ge, In, Sn, Y, Au, Ba, W, Gd, Ga, Pb, Al and Pd.

22. The method as claimed in claim 1, wherein the compound of formula (I) is octabromo mesotetraphenylporphyrin, wherein M is hydrogen or a metal selected from the group consisting of V, Mn, Fe, Ru, Tc, Cr, Pt, Co, Ni, Cu, Zn, Ge, In, Sn, Y, Au, Ba, W, Gd, Ga, Pb, Al and Pd.

\* \* \* \* \*